(12) United States Patent
Michels et al.

(10) Patent No.: US 8,642,595 B2
(45) Date of Patent: Feb. 4, 2014

(54) ANNELLATED 4-(INDAZOLYL)-1,4-DIHYDROPYRIDINE DERIVATIVES AND METHODS OF USE THEREOF

(75) Inventors: Martin Michels, Köln (DE); Markus Follmann, Wülfrath (DE); Alexandros Vakalopoulos, Hilden (DE); Katja Zimmermann, Düsseldorf (DE); Nicole Teusch, Wülfrath (DE); Karen Engel, Wüppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 219 days.

(21) Appl. No.: 12/996,499

(22) PCT Filed: May 29, 2009

(86) PCT No.: PCT/EP2009/003837
§ 371 (c)(1),
(2), (4) Date: Mar. 21, 2011

(87) PCT Pub. No.: WO2009/149836
PCT Pub. Date: Dec. 17, 2009

(65) Prior Publication Data
US 2011/0172221 A1    Jul. 14, 2011

(30) Foreign Application Priority Data
Jun. 9, 2008  (EP) .................................... 08010423

(51) Int. Cl.
*A61K 31/535*  (2006.01)
*C07D 413/04*  (2006.01)
*C07D 413/14*  (2006.01)

(52) U.S. Cl.
USPC ........................ 514/235.2; 544/124; 544/127

(58) Field of Classification Search
USPC ................................ 544/127, 124; 514/235.2
See application file for complete search history.

(56) References Cited

FOREIGN PATENT DOCUMENTS

WO  WO 2008/071451  *  6/2008

OTHER PUBLICATIONS

Cancer and Metastasis Reviews (1998), 17(1), 91-106.*
Science (1999), vol. 286, 531-537.*

* cited by examiner

*Primary Examiner* — Rebecca Anderson

(57) ABSTRACT

This invention relates to novel annellated 4-(indazolyl)-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

19 Claims, No Drawings

ANNELLATED 4-(INDAZOLYL)-1,4-DIHYDROPYRIDINE DERIVATIVES AND METHODS OF USE THEREOF

This invention relates to novel annellated 4-(indazolyl)-1,4-dihydropyridine derivatives having protein tyrosine kinase inhibitory activity, to a process for the manufacture thereof and to the use thereof for the treatment of c-Met-mediated diseases or c-Met-mediated conditions, particularly cancer and other proliferative disorders.

Cancer is one of the most common widespread diseases. Over 4.4 million people worldwide were diagnosed with breast, colon, ovarian, lung or prostate cancer in 2002, and over 2.5 million people died of these devastating diseases (Globocan 2002 Report, http://www-dep.iarc.fr/globocan/down-loads.htm). In the United States alone, over 1.25 million new cases and over 500 000 deaths from cancer were predicted in 2005. The majority of these new cases were expected to be cancers of the colon (~100 000), lung (~170 000), breast (~210 000) and prostate (~230 000). Both the incidence and prevalence of cancer is predicted to increase by approximately 15% over the next ten years, reflecting an average growth rate of 1.4% (American Cancer Society, Cancer Facts and Figures 2005; http://www.cancer.org/docroot/STT/content/STT_1x_Cancer_Facts_Figures_2007.asp).

There are many ways how cancers can arise, which is one of the reasons why their therapy is difficult. One way is the transformation of cells by oncoproteins, which arise from normal cellular proteins by genetic mutations, which results in a non-physiological activation of these proteins. One family of proteins from which a number of oncoproteins derive are tyrosine kinases (e.g. src kinase) and in particular receptor tyrosine kinases (RTKs). In the past two decades, numerous avenues of research have demonstrated the importance of receptor tyrosine kinase (RTK)-mediated signalling in the regulation of mammalian cell growth. Recently, results have been achieved in the clinic with selective small-molecule inhibitors of tyrosine kinases as anti-tumourigenic agents.

The c-Met receptor also is a receptor tyrosine kinase. Its oncogenic potential was identified in the early 1980s, when a mutated Met was isolated from a chemically induced human osteosarcoma cell line which contained the kinase domain of the Met gene fused to a dimerization domain at its N-terminus [C. S. Cooper et al., *Nature* 311: 29-33 (1984)].

The cellular Met protein is a heterodimeric transmembrane protein synthesized as a single chain 190 kd precursor [G. A. Rodrigues et al., *Mol. Cell Biol.* 11: 2962-70 (1991)]. The precursor is cleaved intracellularly after amino acid residue 307 to form the 50 kd α-chain and the 145 kd β-chain, which are connected by disulfide bridges. The α-chain is entirely extracellular, whereas the β-chain spans the plasma membrane. The β-chain is composed of an N-terminal sema domain, which together with the α-chain mediates ligand binding. The remainder of the ectodomain of the β-chain is composed of a cysteine-rich domain and four immunoglobulin domains and is followed by the transmembrane region and the intracellular domain. The intracellular domain contains a juxtamembrane domain, the kinase domain and a C-terminal domain, which mediates the downstream signalling. Upon ligand binding, a dimerization of the receptor is induced, and the kinase domain is activated by a cascade of tyrosine autophosphorylation steps in the juxtamembrane region (Y1003), the activation loop of the kinase (Y1234 and Y1235) and the carboxy-terminal domain (Y1349 and Y1356). Phosphorylated Y1349 and Y1356 comprise the multi-substrate docking site for binding adapter proteins necessary for downstream c-Met signalling [C. Ponzetto et al., *Cell* 77: 261-71 (1994)]. One of the most crucial substrates for c-Met signalling is the scaffolding adaptor protein Gab1, which binds to either Y1349 or Y1356 via an unusual phosphotyrosine binding site (termed mbs: met binding site) which causes a unique prolonged intracellular signal. Another important substrate is the adaptor protein Grb2. Depending on the cellular context, these adaptors mediate the activation of various intracellular signal pathways like the ones signalling via ERKJMAPK, PI3K/Akt, Ras, JNK, STAT, NFκB and β-catenin.

c-Met is uniquely activated by hepatocyte growth factor (HGF), also known as scatter factor, and its splice variants, which is its only known biologically active ligand [L. Naldini et al., *Oncogene* 6: 501-4 (1991)]. HGF has a distinct structure which reveals similarities to proteinases of the plasminogen family. It is composed of an amino-terminal domain followed by four kringle domains and a serine protease homology domain, which is not enzymatically active. Similar to c-Met, HGF is synthesized as an inactive single chain precursor (pro-HGF), which is extracellularly cleaved by serine proteases (e.g. plasminogen activators and coagulation factors) and converted into a disulfide-linked active α- and β-chain heterodimer. HGF binds heparan sulfate proteoglycans with high affinity, which keeps it mainly associated with the extracellular matrix and limits its diffusion. Crystal structure analyses indicate that HGF forms a dimer, which upon binding to c-Met induces dimerization of the receptor.

HGF is expressed by mesenchymal cells, and its binding to c-Met, which is widely expressed in particular in epithelial cells, results in pleiotropic effects in a variety of tissues including epithelial, endothelial, neuronal and hematopoetic cells. The effects generally include one or all of the following phenomena: i) stimulation of mitogenesis; HGF was identified by its mitogenic activity on hepatocytes; ii) stimulation of invasion and migration; in an independent experimental approach, HGF was identified as scatter factor based on its induction of cell motility ("scattering"); and iii) stimulation of morphogenesis (tubulogenesis). HGF induces the formation of branched tubules from canine kidney cells in a collagen matrix. Furthermore, evidence from genetically modified mice and from cell culture experiments indicate that c-Met acts as a survival receptor and protects cells from apoptosis [N. Tomita et al., *Circulation* 107: 1411-1417 (2003); S. Ding et al., *Blood* 101: 4816-4822 (2003); Q. Zeng et al., *J. Biol. Chem.* 277: 25203-25208 (2002); N. Horiguchi et al., *Oncogene* 21: 1791-1799 (2002); A. Bardelli et al., *Embo J.* 15: 6205-6212 (1996); P. Longati et al., *Cell Death Differ.* 3: 23-28 (1996); E. M. Rosen, *Symp. Soc. Exp. Biol.* 47: 227-234 (1993)]. The coordinated execution of these biological processes by HGF results in a specific genetic program which is termed as "invasive growth".

Under normal conditions, c-Met and HGF are essential for embryonic development in mice, in particular for the development of the placenta and the liver and for the directional migration of myoblasts from the somites of the limbs. Genetic disruption of the c-Met or HGF genes results in identical phenotypes which shows their unique interaction. The physiological role of c-Met/HGF in the adult organism is less well understood, but experimental evidence suggests that they are involved in wound healing, tissue regeneration, hemopoiesis and tissue homeostasis.

The identification of the oncoprotein TPR-MET was a first hint that c-Met may play a role in tumourigenesis. Additional substantial evidence is derived from a number of different experimental approaches. Overexpression of c-Met or HGF in human and murine cell lines induces tumourigenicity and a metastatic phenotype when expressed in nude mice. Transgenic overexpression of c-Met or HGF induces tumourigenesis in mice.

Most intriguingly, missense mutations of c-Met or mutations which activate the receptor have been identified in sporadic and hereditary papillary kidney carcinomas (HPRC) as well as in other cancer types like lung, gastric, liver, head and neck, ovarian and brain cancers. Significantly, specific c-Met mutations in HPRC families segregate with disease, forming a causal link between c-Met activation and human cancer [L. Schmidt et al., *Nat. Genet.* 16: 68-73 (1997); B. Thar et al., *Adv. Cancer Res.* 75: 163-201 (1998)]. Activation mutations with the strongest transforming activities are located in the activation loop (D1228N/H and Y1230H/D/C) and in the adjacent P+1 loop (M1250T). Additional weaker mutations have been found near the catalytic loop and within the A lobe of the kinase domain. Furthermore, some mutations in the juxtamembrane domain of c-Met have been observed in lung tumours which do not directly activate the kinase, but rather stabilize the protein by rendering it resistant to ubiquitination and subsequent degradation [M. Kong-Beltran et al., *Cancer Res.* 66: 283-9 (2006); T. E. Taher et al., *J. Immunol.* 169: 3793-800 (2002); P. Peschard et al., *Mol. Cell* 8: 995-1004 (2001)]. Interestingly, somatic mutations of c-Met are associated with increased aggressiveness and extensive metastases in various cancers. While the frequency of germ line and somatic mutations is low (below 5%), other major mechanisms have been observed leading to a deregulation of the c-Met signalling, in the absence of mutations, by paracrine or autocrine mechanisms. Paracrine activation has been observed in tumours which are derived from mesenchymal cells, like osteosarcomas or rhabdomyosarcomas, which physiologically produce HGF, and in glioblastomas and mamma carcinomas which are of ectodermal origin.

However, the most frequent cases are carcinomas where c-Met is overexpressed as observed in carcinomas of the colon, pancreas, stomach, breast, prostate, ovary and liver. Overexpression may arise, for example, by gene amplification as observed in gastric and lung tumour cell lines. Very recently, overexpression of c-Met was detected in lung tumour cell lines which acquired resistance to EGF receptor inhibition [J. A. Engelmann et al., *Science* 316: 1039-1043 (2007)]. Some epithelial tumours that overexpress c-Met also co-express HGF, resulting in an autocrine c-MetIHGF stimulatory loop and thereby circumventing the need for stromal cell-derived HGF.

In general, it has been found that aberrant activation of c-Met in human cancer is typically associated with a poor prognosis, regardless of the specific mechanism [J. G. Christensen et al., *Cancer Lett.* 225: 1-26 (2005)].

In summary, a great number of in vitro and in vivo studies have been performed that validate c-Met as an important cancer target, and a comprehensive list can be viewed at http://www.vai.org/met [C. Birchmeier et al., *Nat. Rev. Mol. Cell Biol.* 4: 915-25 (2003)]. Several strategies have been followed to attenuate aberrant Met signalling in human tumours including HPF antagonists and small molecule inhibitors, amongst others. A number of small molecule inhibitors are currently in clinical development, such as ARQ-197 (Arqule), XL-880 (Exelixis), and PH-2341066 (Pfizer); they have recently been reviewed [J. J. Cui, *Expert Opin. Ther. Patents* 17: 1035-45 (2007)].

The technical problem to be solved according to the present invention may therefore be seen in providing alternative compounds having an inhibitory activity on the c-Met kinase, thus offering new therapeutic options for the treatment of c-Met-mediated diseases, particularly cancer and other proliferative disorders.

4-Heteroaryl-1,4-dihydropyridine derivatives and uses thereof for the treatment of various diseases are described in, inter al., WO 2004/033444-A1, WO 2005/016885-A2, WO 2006/066011-A2 and WO 2007/051062-A2. In WO 91/18906-A1, WO 93/11133-A1 and WO 93/11134-A1, thiazolo-annellated 1,4-dihydropyridines with anti-asthmatic and anti-inflammatory activities have been disclosed. In the interim, 1,4-dihydropyridine-type compounds with c-Met kinase inhibitory activity have been described in WO 2008/071451-A1.

In one aspect, the present invention relates to annellated 4-(indazolyl)-1,4-dihydropyridine derivatives of the general formula (I)

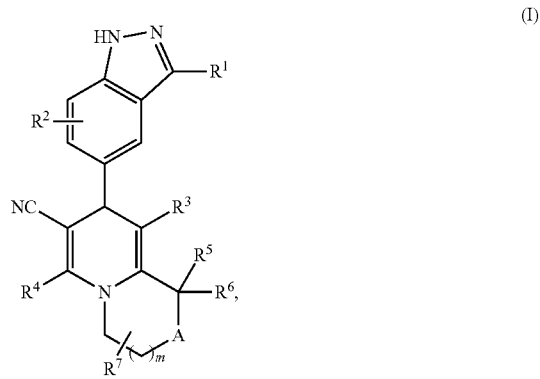

wherein
$R^1$ is selected from the group consisting of $(C_1-C_6)$-alkyl, $(C_3-C_7)$-cycloalkyl, phenyl, 4- to 7-membered heterocycloalkyl and 5- to 10-membered heteroaryl, wherein
(i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl,
and
(ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl,
wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^1$ is a group of the formula $-NR^8R^9$, $-C(=O)-NR^{10}R^{11}$, $-SO_2-NR^{12}R^{13}$, $-NR^{14}-C(=O)-R^{15}$, $-NR^{16}-SO_2-R^{17}$, $-OR^{18}$ or $-S(=O)_n-R^{19}$, wherein n is 0, 1 or 2, $R^8$, $R^9$, $R^{10}$, $R^{11}$, $R^{12}$ and $R^{13}$ are independently selected from the group consisting of hydrogen, $(C_1-C_6)$-alkyl, $(C_3-C_7)$-cycloalkyl, phenyl, 4- to 7-membered heterocycloalkyl and 5- to 10-membered heteroaryl, wherein (i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^8$ and $R^9$, $R^{10}$ and $R^{11}$, $R^{12}$ and $R^{13}$ in pairs are joined and, taken together with the nitrogen atom to which each pair is attached, form a 4- to 7-membered heterocycloalkyl ring, which may contain a second ring heteroatom selected from N, O and S, and which is optionally substituted with one or two substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl, $R^{14}$ and $R^{16}$ are hydrogen or $(C_1-C_6)$-alkyl, $R^{15}$, $R^{17}$, $R^{18}$ and $R^{19}$ are each selected from the group consisting of $(C_1-C_6)$-alkyl, $(C_3-C_7)$-cycloalkyl, phenyl, 4- to 7-membered heterocycloalkyl and 5- to 10-membered heteroaryl, wherein (i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^{16}$ and $R^{17}$ are joined and, taken together with the nitrogen atom and $SO_2$ group to which they are attached, form a heterocyclic moiety of the formula

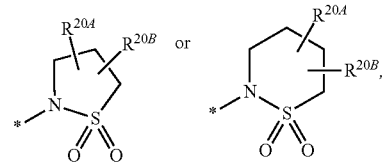

wherein * denotes the point of attachment to the indazole moiety, and $R^{20A}$ and $R^{20B}$ are independently selected from the group consisting of hydrogen, fluoro and $(C_1-C_4)$-alkyl, $R^2$ is hydrogen, fluoro, chloro or methyl, $R^3$ is cyano or a group of the formula $-C(=O)-OR^{21}$ or $-C(=O)-NR^{22}R^{23}$, wherein $R^{21}$ is $(C_1-C_6)$-alkyl optionally substituted with $(C_3-C_7)$-cycloalkyl, or is $(C_4-C_7)$-cycloalkyl, and $R^{22}$ and $R^{23}$ are independently selected from the group consisting of hydrogen, $(C_1-C_6)$-alkyl and $(C_3-C_7)$-cycloalkyl, wherein said $(C_1-C_6)$-alkyl is optionally substituted with $(C_3-C_7)$-cycloalkyl, $R^4$ is $(C_1-C_4)$-alkyl optionally substituted with up to three fluoro atoms, or is cyclopropyl or amino, $R^5$ is hydrogen, $(C_1-C_6)$-alkyl or $(C_3-C_7)$-cycloalkyl, wherein said $(C_1-C_6)$-alkyl is optionally substituted with up to three fluoro atoms or with one or two substituents independently selected from the group consisting of hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocycloalkyl, $R^6$ and $R^7$ are independently hydrogen or $(C_1-C_4)$-alkyl, and either (a)

A is O, S, S(=O) or $S(=O)_2$ and m is 1 or 2, or (b)

A is $N(R^{24})$, wherein $R^{24}$ is hydrogen, $(C_1-C_6)$-alkyl, $(C_3-C_7)$-cycloalkyl or $(C_1-C_6)$-alkylcarbonyl, wherein said $(C_1-C_6)$-alkyl, $(C_3-C_7)$-cycloalkyl and $(C_1-C_6)$-alkylcarbonyl are optionally substituted with one or two substituents independently selected from the group consisting of hydroxy, ($C_1$-$C_4$)-alkoxy, amino, mono-($C_1$-$C_4$)-alkylamino and di-($C_1$-$C_4$)-alkylamino, and m is 1 or 2, in which case $R^5$ and $R^6$, in addition to the meanings specified above, may also be taken together and form an oxo group, or (c)

A is —C(=O)—N($R^{25}$)—**, wherein

** denotes the point of attachment to the $CR^5R^6$ group, and $R^{25}$ is hydrogen, ($C_1$-$C_6$)-alkyl or ($C_3$-$C_7$)-cycloalkyl, wherein said ($C_1$-$C_6$)-alkyl and ($C_3$-$C_7$)-cycloalkyl are optionally substituted with one or two substituents independently selected from the group consisting of hydroxy, ($C_1$-$C_4$)-alkoxy, amino, mono-($C_1$-$C_4$)-alkylamino and di-($C_1$-$C_4$)-alkylamino, and m is 0 or 1.

The compounds according to this invention can also be present in the form of their salts, hydrates and/or solvates.

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19).

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, N-methylpiperidine, dihydroabietylamine, arginine, lysine, and ethylenediamine.

Hydrates of the compounds of the invention or their salts are stoichiometric compositions of the compounds with water, such as, for example, hemi-, mono-, or dihydrates.

Solvates of the compounds of the invention or their salts are stoichiometric compositions of the compounds with solvents.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S) configuration.

It will also be appreciated that when two or more asymmetric centers are present in the compounds of the invention, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the invention.

Geometric isomers by nature of substituents about a double bond or a ring may be present in cis (=Z-) or trans (=E-) form, and both isomeric forms are encompassed within the scope of this invention.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

Unless otherwise stated, the following definitions apply for the substituents and residues used throughout this specification and claims:

Alkyl in general represents a straight-chain or branched saturated hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, neopentyl, hexyl, isohexyl. The same applies to radicals such as alkoxy, alkylamino, alkylcarbonyl, and the like.

Alkoxy illustratively and preferably represents methoxy, ethoxy, n-propoxy, isopropoxy, n-butoxy and tert.-butoxy. The same applies to radicals such as alkoxycarbonyl.

Alkylcarbonyl in general represents a straight-chain or branched alkyl radical having 1 to 6, preferably 1 to 4 carbon atoms which is bonded via a carbonyl group to the rest of the molecule. Non-limiting examples include acetyl, n-propionyl, n-butyryl, isobutyryl, n-pentanoyl, pivaloyl and n-hexanoyl.

Alkoxycarbonyl illustratively and preferably represents methoxycarbonyl, ethoxycarbonyl, n-propoxycarbonyl, isopropoxycarbonyl, n-butoxycarbonyl and tert.-butoxycarbonyl.

Monoalkylamino in general represents an amino radical having one alkyl residue attached to the nitrogen atom. Non-limiting examples include methylamino, ethylamino, n-propylamino, isopropylamino, n-butylamino, tert.-butylamino. The same applies to radicals such as monoalkylaminocarbonyl.

Dialkylamino in general represents an amino radical having two independently selected alkyl residues attached to the nitrogen atom. Non-limiting examples include N,N-dimethylamino, N,N-diethylamino, N,N-diisopropylamino, N-ethyl-N-methylamino, N-methyl-N-n-propylamino, N-isopropyl-N-n-propylamino, N-tert.-butyl-N-methylamino. The same applies to radicals such as dialkylaminocarbonyl.

Monoalkylaminocarbonyl illustratively and preferably represents methylaminocarbonyl, ethylaminocarbonyl, n-propylaminocarbonyl, isopropylaminocarbonyl, n-butylaminocarbonyl and tert.-butylaminocarbonyl.

Dialkylaminocarbonyl illustratively and preferably represents N,N-dimethylaminocarbonyl, N,N-diethylaminocarbonyl, N,N-diisopropylaminocarbonyl, N-ethyl-N-methylaminocarbonyl, N-methyl-N-n-propylaminocarbonyl, N-isopropyl-N-n-propylaminocarbonyl and N-tert.-butyl-N-methylaminocarbonyl.

Cycloalkyl in general represents a mono- or bicyclic saturated hydrocarbon radical having 3 to 7, preferably 3 to 6 carbon atoms. Preference is given to monocyclic cycloalkyl radicals. Non-limiting examples include cyclopropyl, cyclobutyl, cyclopentyl, cyclohexyl, cycloheptyl, bicyclo-[2.2.1]heptyl.

Heterocycloalkyl in general represents a mono- or bicyclic, saturated heterocyclic radical having a total number of 4 to 7, preferably 4 to 6 ring atoms, including 3 to 6, preferably 3 to 5 carbon atoms and up to 2 heteroatoms and/or hetero-groups independently selected from the group consisting of N, O, S, SO and $SO_2$, which ring system can be bonded via a ring carbon atom or, if possible, via a ring nitrogen atom. Non-limiting examples include azetidinyl, oxetanyl, thietanyl, pyrrolidinyl, pyrazolidinyl, tetrahydrofuranyl, thiolanyl, sulfolanyl, 1,3-dioxolanyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, morpholinyl, thiomorpholinyl, 1,1-dioxidothiomorpholinyl, perhydroazepinyl, perhydro-1,4-diazepinyl, perhydro-1,4-oxazepinyl, 7-azabicyclo[2.2.1]heptyl, 3-azabicyclo-[3.2.0]heptyl, 7-azabicyclo[4.1.0]heptyl, 2,5-diazabicyclo[2.2.1]heptyl, 2-oxa-5-azabicyclo[2.2.1]-heptyl. Particular preference is given to 5- or 6-membered monocyclic heterocycloalkyl radicals having up to 2 heteroatoms selected from the group consisting of N, O and S, such as illustratively and preferably tetrahydrofuranyl, 1,3-dioxolanyl, pyrrolidinyl, tetrahydropyranyl, 1,4-dioxanyl, piperidinyl, piperazinyl, morpholinyl, and thiomorpholinyl.

Heteroaryl in general represents a mono- or bicyclic, aromatic heterocyclic radical having a total number of 5 to 10 ring atoms, including 2 to 9 carbon atoms and up to 3 heteroatoms independently selected from the group consisting of N, O and S, which ring system can be bonded via a ring carbon atom or, if possible, via a ring nitrogen atom. Non-limiting examples include furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, benzothiadiazolyl, indolyl, isoindolyl, indazolyl, quinolinyl, isoquinolinyl, naphthyridinyl, quinazolinyl, quinoxalinyl, phthalazinyl, imidazopyridinyl, pyrazolopyridinyl, pyrrolopyrimidinyl. Preference is given to 6-membered heteroaryl radicals having up to 2 nitrogen atoms, such as pyridyl, pyrimidyl, pyridazinyl and pyrazinyl, and to 5-membered heteroaryl radicals having up to 2 heteroatoms selected from the group consisting of N, O and S, such as illustratively and preferably thienyl, furyl, pyrrolyl, pyrazolyl, imidazolyl, thiazolyl, oxazolyl, isothiazolyl, and isoxazolyl.

Halogen represents radicals of fluorine, chlorine, bromine and iodine. Preference is given to radicals of fluorine and chlorine.

Oxo represents a doubly bonded oxygen atom.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

In a preferred embodiment, the present invention relates to compounds of general formula (I), wherein $R^1$ is selected from the group consisting of $(C_1-C_6)$-alkyl, $(C_3-C_6)$-cycloalkyl, phenyl, 4- to 6-membered heterocycloalkyl and 5- or 6-membered heteroaryl, wherein
  (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl,
  and
  (ii) said $(C_1-C_6)$-alkyl is optionally substituted with one or two substituents independently selected from the group consisting of hydroxy, $(C_1-C_4)$-alkoxy, amino, mono-$(C_1-C_4)$-alkylamino, di-$(C_1-C_4)$-alkylamino, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl,
    wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^1$ is a group of the formula —$NR^8R^9$, —C(=O)—$NR^{10}R^{11}$, —$SO_2$—$NR^{12}R^{13}$, —$NR^{14}$—C(=O)—$R^{15}$, —$NR^{16}$—$SO_2$—$R^{17}$, —$OR^{18}$ or —S(=O)$_n$—$R^{19}$, wherein
  n is 0 or 2,
  $R^8$, $R^{10}$ and $R^{12}$ are each hydrogen or $(C_1-C_4)$-alkyl which is optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino,
  $R^9$, $R^{11}$ and $R^{13}$ are each selected from the group consisting of hydrogen, $(C_1-C_6)$-alkyl, $(C_3-C_6)$-cycloalkyl, phenyl, 4- to 6-membered heterocycloalkyl and 5- or 6-membered heteroaryl, wherein
    (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
    and
    (ii) said $(C_1-C_6)$-alkyl is optionally substituted with one or two substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl,
      wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^8$ and $R^9$, $R^{10}$ and $R^{11}$, $R^{12}$ and $R^{13}$ in pairs are joined and, taken together with the nitrogen atom to which each pair is attached, form a 4- to 6-membered heterocycloalkyl ring, which may contain a second ring heteroatom selected from N, O and S, and which is optionally substituted with one or two substituents independently selected from the group consisting of $(C_1-C_4)$-alkyl, oxo, hydroxy, $(C_1-C_4)$-alkoxy, amino, mono-$(C_1-C_4)$-alkylamino and di-$(C_1-C_4)$-alkylamino, $R^{14}$ and $R^{16}$ are hydrogen or $(C_1-C_4)$-alkyl, $R^{15}$, $R^{17}$, $R^{18}$ and $R^{19}$ are each selected from the group consisting of $(C_1-C_6)$-alkyl, $(C_3-C_6)$-cycloalkyl, phenyl, 4- to 6-membered heterocycloalkyl and 5- or 6-membered heteroaryl, wherein
  (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
  and
  (ii) said $(C_1-C_6)$-alkyl is optionally substituted with one or two substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl,
    wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino, or $R^{16}$ and $R^{17}$ are joined and, taken together with the nitrogen atom and $SO_2$ group to which they are attached, form a heterocyclic moiety of the formula

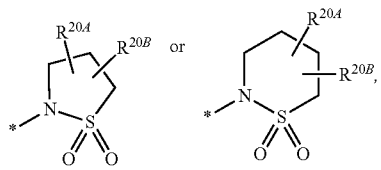

wherein * denotes the point of attachment to the indazole moiety,
and
$R^{20A}$ and $R^{20B}$ are independently hydrogen or methyl, $R^2$ is hydrogen, fluoro or chloro, $R^3$ is cyano or a group of the formula —C(=O)—$OR^{21}$ or —C(=O)—$NR^{22}R^{23}$, wherein
  $R^{21}$ is $(C_1-C_4)$-alkyl,
  and
  $R^{22}$ and $R^{23}$ are independently selected from the group consisting of hydrogen and $(C_1-C_4)$-alkyl, $R^4$ is $(C_1-C_4)$-alkyl optionally substituted with up to three fluoro atoms, or is amino, $R^5$ is hydrogen or $(C_1-C_4)$-alkyl optionally substituted with one or two substituents independently selected from the group consisting of hydroxy, $(C_1-C_4)$-alkoxy, amino, mono-$(C_1-C_4)$-alkylamino, di-$(C_1-C_4)$-alkylamino and 4- to 6-membered heterocycloalkyl, $R^6$ and $R^7$ are independently hydrogen or methyl, and either (a)
  A is O, S or S(=O)$_2$
  and
  m is 1 or 2,
or (b)
  A is N($R^{24}$), wherein
    $R^{24}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, mono-$(C_1-C_4)$-alkylamino and di-$(C_1-C_4)$-alkylamino,
  and
  m is 1 or 2,
  in which case
  $R^5$ and $R^6$, in addition to the meanings specified above, may also be taken together and form an oxo group,
or (c)
  A is —C(=O)—N($R^{25}$)—**, wherein
    ** denotes the point of attachment to the $CR^5R^6$ group,
    and
    $R^{25}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, mono-$(C_1-C_4)$-alkylamino and di-$(C_1-C_4)$-alkylamino,
  and
  m is 0 or 1.

In a further preferred embodiment, the present invention relates to compounds of general formula (I), wherein $R^2$ is hydrogen or fluoro.

In another preferred embodiment, the present invention relates to compounds of general formula (I), wherein $R^3$ is cyano.

In another likewise preferred embodiment, the present invention relates to compounds of general formula (I), wherein $R^4$ is methyl, difluoromethyl, trifluoromethyl or amino.

In another likewise preferred embodiment, the present invention relates to compounds of general formula (I), wherein both $R^6$ and $R^7$ are hydrogen.

In another likewise preferred embodiment, the present invention relates to compounds of general formula (I), wherein A is O, and m is 1.

In another likewise preferred embodiment, the present invention relates to compounds of general formula (I), wherein A is N($R^{24}$), and m is 1.

In another likewise preferred embodiment, the present invention relates to compounds of general formula (I), wherein A is —C(=O)—N($R^{25}$)—, wherein  denotes the point of attachment to the $CR^5R^6$ group, and m is 0.

In a particularly preferred embodiment, the present invention relates to compounds of general formula (I), wherein $R^1$ is selected from the group consisting of $(C_1-C_4)$-alkyl, $(C_3-C_6)$-cycloalkyl and 5- or 6-membered heterocycloalkyl, wherein
  (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino,
  and
  (ii) said $(C_1-C_4)$-alkyl is optionally substituted with one or two substituents independently selected from the group consisting of hydroxy, methoxy, ethoxy, amino, methylamino, ethylamino, dimethylamino, diethylamino, $(C_3-C_6)$-cycloalkyl and 5- or 6-membered heterocycloalkyl,
wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or $R^1$ is a group of the formula $-NR^8R^9$, $-C(=O)-NR^{10}R^{11}$, $-SO_2-NR^{12}R^{13}$, $-NR^{14}-C(=O)-R^{15}$, $-NR^{16}-SO_2-R^{17}$, $-OR^{18}$ or $-S(=O)_n-R^{19}$, wherein
n is 0 or 2,
$R^8$, $R^{10}$ and $R^{12}$ are each hydrogen or $(C_1-C_4)$-alkyl which is optionally substituted with hydroxy, methoxy, ethoxy, amino, methylamino, ethylamino, dimethylamino or diethylamino,
$R^9$, $R^{11}$ and $R^{13}$ are each selected from the group consisting of hydrogen, $(C_1-C_4)$-alkyl, $(C_3-C_6)$-cycloalkyl and 5- or 6-membered heterocycloalkyl, wherein
(i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino,
and
(ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl,
wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or $R^8$ and $R^9$, $R^{10}$ and $R^{11}$, $R^{12}$ and $R^{13}$ in pairs are joined and, taken together with the nitrogen atom to which each pair is attached, form a 5- or 6-membered heterocycloalkyl ring, which may contain a second ring heteroatom selected from N and O, and which is optionally substituted with one or two substituents independently selected from the group consisting of methyl, ethyl, oxo, hydroxy, methoxy, ethoxy, amino, methylamino, ethylamino, dimethylamino and diethylamino,
$R^{14}$ and $R^{16}$ are hydrogen, methyl or ethyl,
$R^{15}$, $R^{17}$, $R^{18}$ and $R^{19}$ are each selected from the group consisting of $(C_1-C_4)$-alkyl, $(C_3-C_6)$-cycloalkyl and 5- or 6-membered heterocycloalkyl, wherein
(i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino,
and
(ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl,
wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or $R^{16}$ and $R^{17}$ are joined and, taken together with the nitrogen atom and $SO_2$ group to which they are attached, form a heterocyclic moiety of the formula

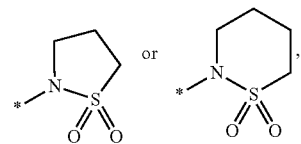 [SMILES: *N1CCCS1(=O)=O ; "or" ; *N1CCCCS1(=O)=O ; ","]

wherein * denotes the point of attachment to the indazole moiety,
$R^2$ is hydrogen or fluoro,
$R^3$ is cyano,
$R^4$ is methyl, trifluoromethyl or amino,
$R^5$ is hydrogen or $(C_1-C_4)$-alkyl optionally substituted with one or two substituents independently selected from the group consisting of hydroxy, amino, methylamino, ethylamino, dimethylamino and diethylamino,
$R^6$ and $R^7$ are hydrogen,
and either (a)
A is O
and
m is 1,
or (b)
A is $N(R^{24})$, wherein
$R^{24}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, methylamino, ethylamino, dimethylamino and diethylamino,
and
m is 1,
in which case
$R^5$ and $R^6$, in addition to the meanings specified above, may also be taken together and form an oxo group,
or (c)
A is $-C(=O)-N(R^{25})-$**, wherein
** denotes the point of attachment to the $CR^5R^6$ group,
and
$R^{25}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, methylamino, ethylamino, dimethylamino and diethylamino,
and
m is 0.

In a further distinct embodiment, the present invention relates to compounds of general formula (I), wherein
$R^1$ is selected from the group consisting of $(C_1-C_4)$-alkyl, phenyl and pyridyl, wherein said phenyl and pyridyl are optionally substituted with one or two substituents independently selected from the group consisting of fluoro, chloro, methyl and trifluoromethyl, $R^2$ is hydrogen or fluoro,
$R^3$ is cyano,
$R^4$ is methyl,
$R^5$, $R^6$ and $R^7$ are hydrogen,
A is O,
and
m is 1.

The definitions of residues indicated specifically in the respective combinations or preferred combinations of residues are also replaced as desired by definitions of residues of other combinations, irrespective of the particular combinations indicated for the residues. Combinations of two or more of the abovementioned preferred ranges are particularly preferred.

In another embodiment, the present invention relates to a process for preparing the compounds of general formula (I), characterized in that a compound of formula (II)

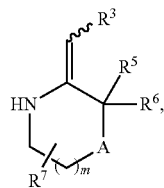
(II)

wherein m, A, $R^3$, $R^5$, $R^6$ and $R^7$ have the meanings described above,
is reacted in a protic solvent with acid catalysis either
[A] with a compound of formula (III)

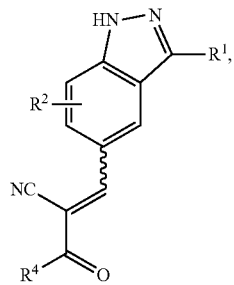
(III)

wherein $R^1$, $R^2$ and $R^4$ have the meanings described above,
to give compounds of formula (I) directly,
or
[B] with a compound of formula (IV)

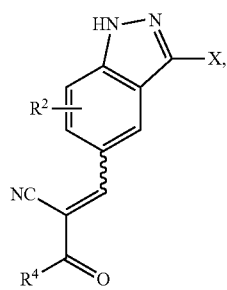
(IV)

wherein $R^2$ and $R^4$ have the meanings described above,
and
X represents a leaving group such as chloro, bromo or iodo,
to yield an intermediate compound of formula (V)

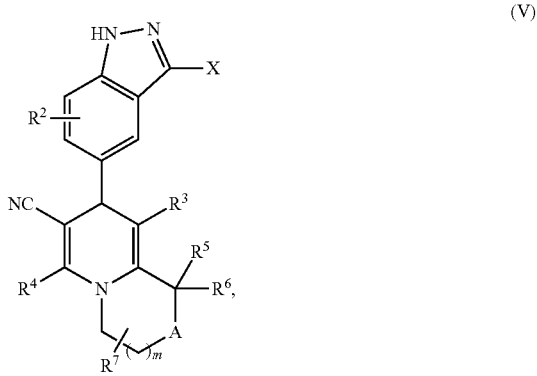
(V)

wherein m, A, X, $R^2$, $R^3$, $R^4$, $R^5$, $R^6$ and $R^7$ have the meanings described above,
which is then coupled under transition metal catalysis either
[B-1] with a compound of formula (VI)

wherein
$R^{1A}$ represents an N-, O- or S-linked $R^1$ residue of the formula —$NR^8R^9$, —$OR^{18}$ or —$S(=O)_n$—$R^{19}$, respectively, as defined above,
to give a compound of formula (I-A)

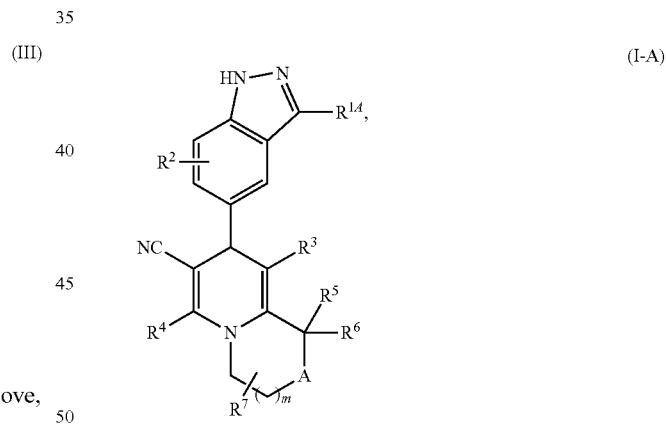
(I-A)

wherein m, A, $R^{1A}$, $R^2$, $R^3$, $R^4$, $R^5$, $R^6$ and $R^7$ have the meanings described above,
or
[B-2] with a compound of formula (XIV)

wherein
$R^{1B}$ represents an optionally substituted C-linked $R^1$ residue selected from the group consisting of ($C_1$-$C_6$)-alkyl, ($C_3$-$C_7$)-cycloalkyl, phenyl, 4- to 7-membered heterocycloalkyl and 5- to 10-membered heteroaryl, as defined above,
and
M represents a —$B(OR^{26})_2$, —MgHal, —ZnHal or —$Sn(R^{27})_3$ group, wherein
Hal is halogen, especially chloro, bromo or iodo, $R^{26}$ is hydrogen or $(C_1-C_4)$-alkyl, or both $R^{26}$ residues together form a —$(CH_2)_2$—, —$C(CH_3)_2$—$C(CH_3)_2$—, —$(CH_2)_3$— or —$CH_2$—$C(CH_3)_2$—$CH_2$— bridge,
and
$R^{27}$ is $(C_1-C_4)$-alkyl,
to yield a compound of formula (I-B)

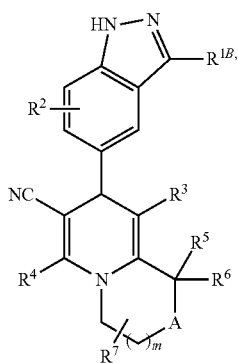

(I-B)

wherein m, A, $R^{1B}$, $R^2$, $R^3$, $R^4$, $R^5$, $R^6$ and $R^7$ have the meanings described above, optionally followed, where appropriate, by (i) separating the compounds (I), (I-A) and (I-B) into their respective enantiomers and/or diastereomers, preferably using chromatographic methods, and/or (ii) converting the compounds (I), (I-A) and (I-B) into their respective hydrates, solvates, salts and/or hydrates or solvates of the salts by treatment with the corresponding solvents and/or acids or bases.

Protic solvents suitable for process steps (II)+(III)→(I) and (II)+(IV)→(V) are, for example, alcohols such as methanol, ethanol, n-propanol, isopropanol, n-butanol and tert-butanol, or acetic acid. It is likewise possible to use mixtures of these solvents. Examples of suitable acid catalysts for said reactions are acetic acid, trifluoroacetic acid, methanesulfonic acid and p-toluenesulfonic acid. Preferably, acetic acid is simultaneously used as solvent and acid catalyst.

The reactions (II)+(III)→(I) and (II)+(IV)→(V) are generally carried out at a temperature range from +20° C. to +120° C., preferably from +65° C. to +120° C., under atmospheric pressure.

Inert solvents suitable for process steps (V)+(VI)→(I-A) and (V)+(XIV)→(I-B) include, for example, aromatic hydrocarbons such as benzene, toluene and xylene, ethers such as diethyl ether, diisopropyl ether, methyl tert-butyl ether, 1,2-dimethoxyethane, tetrahydrofuran, 1,4-dioxane and bis-(2-methoxyethyl)-ether, or dipolar-aprotic solvents such as acetonitrile, dimethylsulfoxide (DMSO), N,N-dimethylformamide (DMF), N,N-dimethylacetamide (DMA), N-methylpyrrolidinone (NMP), N,N'-dimethylpropylene urea (DMPU) and pyridine. It is also possible to use mixtures of these solvents. Preferred solvents are toluene, tetrahydrofuran, 1,4-dioxane, N,N-dimethylformamide and mixtures thereof.

The coupling reactions (V)+(VI)→(I-A) and (V)+(XIV)→(I-B) are carried out with the aid of a transition metal catalyst. Suitable for this purpose are in particular copper catalysts such as copper(I) iodide, and palladium catalysts such as palladium on activated charcoal, bis(dibenzylideneacetone)-palladium(0), tris(dibenzylideneacetone)-dipalladium(0), tetrakis(triphenylphosphine)-palladium(0), bis(triphenylphosphine)-palladium(II) chloride, bis(acetonitrile)-palladium(II) chloride, [1,1'-bis(diphenylphosphino)ferrocene]-palladium(II) chloride or palladium(II) acetate, optionally in combination with additional phosphane ligands such as, for example, dicyclohexyl-[2',4',6'-tris(1-methylethyl)biphenyl-2-yl]phosphane (XPHOS) or 4,5-bis(diphenylphosphino)-9,9-dimethylxanthene (Xantphos) [see, for example, J. Hassan et al., *Chem. Rev.* 102, 1359-1469 (2002); V. Farina, V. Krishnamurthy and W. J. Scott, in: *The Stille Reaction*, Wiley, New York, 1998].

Process steps (V)+(VI)→(I-A) and (V)+(XIV)→(I-B) are usually performed at a temperature range from +20° C. to +200° C., preferably from +80° C. to +180° C., at atmospheric pressure. However, it is also possible to run these reactions at elevated pressure or at reduced pressure (for example in a range from 0.5 to 5 bar). Furthermore, said reactions can advantageously be carried out by means of concomitant microwave irradiation.

The compounds of formula (II) may be prepared starting from a lactam of formula (VII)

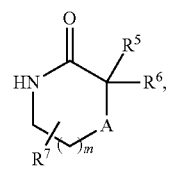

(VII)

wherein m, A, $R^5$, $R^6$ and $R^7$ have the meanings described above, which is first condensed via its lactim ether derivative of formula (VIII)

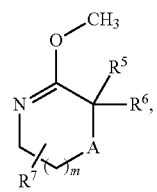

(VIII)

wherein m, A, $R^5$, $R^6$ and $R^7$ have the meanings described above, with a cyanoacetate or malonate of formula (IX)

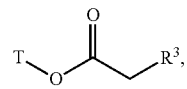

(IX)

wherein $R^3$ has the meaning described above,
and
T represents $(C_1-C_4)$-alkyl or benzyl, to give a compound of formula (X)

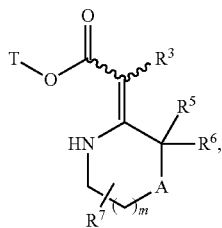

wherein m, A, T, $R^3$, $R^5$, $R^6$ and $R^7$ have the meanings described above,
which then, upon ester cleavage and decarboxylation, yields the enamine derivative of formula (II). This intermediate is employed in the subsequent reaction with compound am or (IV), respectively, preferably using a one-pot procedure, i.e. without further isolation and purification.

The compounds of formula (III) are readily accessible by acid/base-catalyzed condensation of an aldehyde of formula (XI)

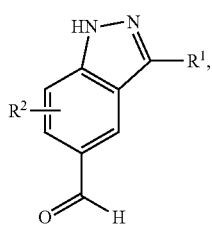

wherein $R^1$ and $R^2$ have the meanings described above, with a cyanoenolate of formula (XII)

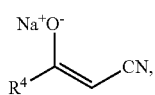

wherein $R^4$ has the meaning described above.

The compounds of formula (IV) can be prepared analogously by employing an aldehyde of formula (XIII)

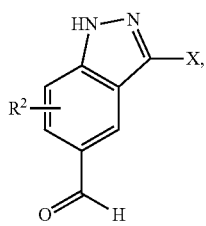

wherein X and $R^2$ have the meanings described above, in the condensation reaction.

The compounds of the formulae (VI), (VII), (IX), (XI), (XII), (XIII) and (XIV) are either commercially available, known from the literature, or can be prepared from readily available starting materials by adaptation of standard methods described in the literature [for the synthesis of indazole intermediates, see, for example, G. Luo et al., *J. Org. Chem.* 71, 5392 (2006), and procedures described in WO 2007/124288-A1, WO 2005/056550-A2, US 2005/0227968-A1 and EP 1 510 516-A1; for the synthesis of lactam precursors of the formula (VII) type, see, for example, M. L. Fan et al., *Synthesis* 14, 2286 (2006), M. L. Fan et al., *Tetrahedron* 62, 6782 (2006), E. Pfeil et al., *Angew. Chem. Int. Ed.* 6, 178 (1967), G. P. Pollini et al., *Tetrahedron Lett.* 46, 3699 (2005), and procedures described in WO 2004/083173-A2 and WO 03/061652-A1].

The preparation of the compounds of the invention can be illustrated by means of the following synthesis schemes 1-3. More detailed procedures are presented below in the experimental section describing the Examples.

Scheme 1

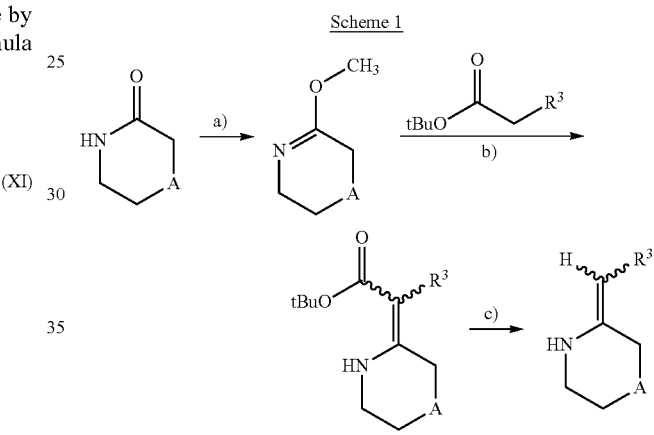

[a]: $Me_3O^+ BF_4^-$, $Na_2CO_3$, $CH_2Cl_2$, 0° C.; b): THF, reflux; c): 6 M aq. HCl, 100° C.].

Scheme 2

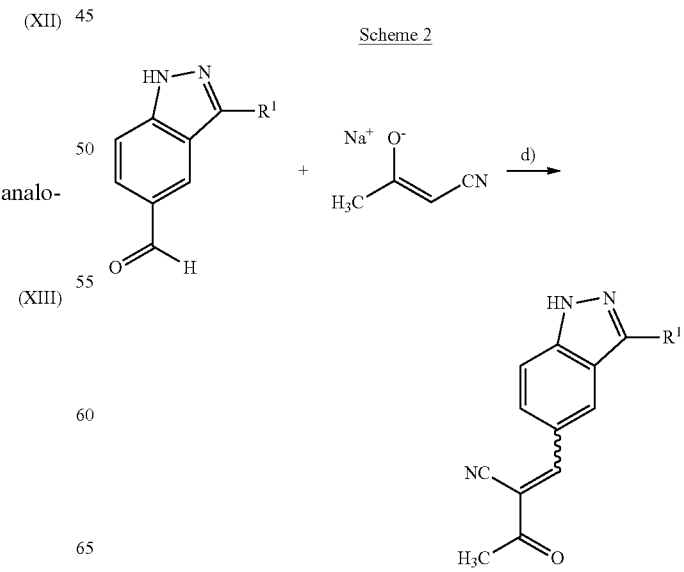

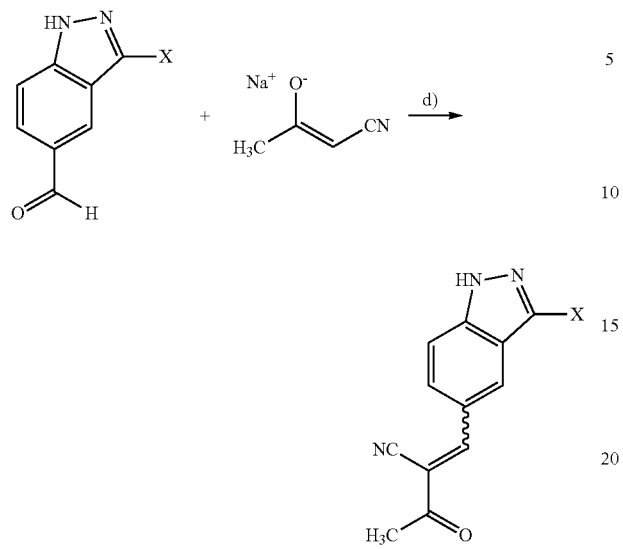

[d]: acetic acid/piperidine, CH$_2$Cl$_2$, 4 Å molecular sieve, reflux].

Scheme 3

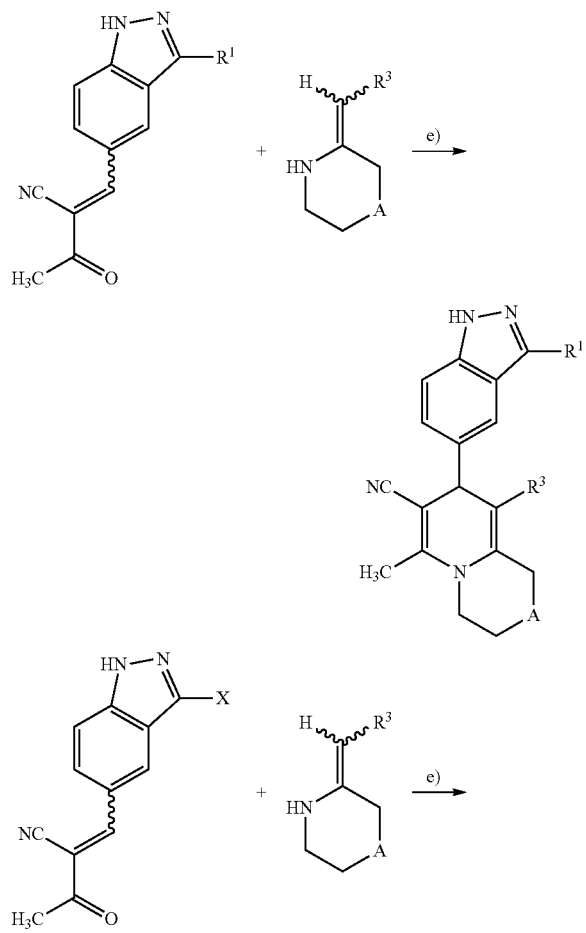

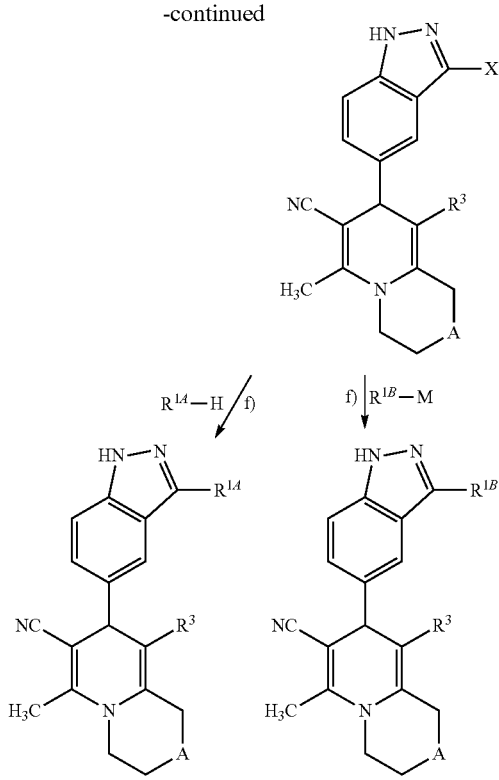

[e]: acetic acid, 100° C.; f): Cu(I), Pd(0) or Pd(II) catalyst, 1,4-dioxane or DMF, microwave irradiation, 100-180° C.].

Methods of Use

The compounds of the present invention may be used to inhibit the activity or expression of receptor tyrosine kinases, particularly of the c-Met receptor tyrosine kinase. Therefore, the compounds of formula (I) are expected to be valuable as therapeutic agents. Accordingly, in another embodiment, the present invention provides a method of treating disorders relating to or mediated by c-Met kinase activity in a patient in need of such treatment, comprising administering to the patient an effective amount of a compound of formula (I) as defined above. In certain embodiments, the disorders relating to c-Met kinase activity are cell proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by c-Met" shall include diseases associated with or implicating c-Met activity, for example the hyperactivity of c-Met, and conditions that accompany with these diseases. Examples of "disorders relating to or mediated by c-Met" include disorders resulting from overstimulation of c-Met due to abnormally high amount of c-Met or mutations in c-Met, or disorders resulting from abnormally high amount of c-Met activity due to abnormally high amount of c-Met or mutations in c-Met.

The term "hyperactivity of c-Met" refers to either c-Met expression in cells which normally do not express c-Met or c-Met activity by cells which normally do not possess active c-Met or increased c-Met expression leading to unwanted cell proliferation or mutations leading to constitutive activation of c-Met.

The term "cell proliferative disorder" includes disorders involving the undesired or uncontrolled proliferation of a cell. The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, isomer, polymorph, metabolite, hydrate or solvate thereof which is effective to treat or prevent the disorder.

Cell proliferative or hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

Compounds of formula (I) may be administered as the sole pharmaceutical agent or in combination with one or more additional therapeutic agents where the combination causes no unacceptable adverse effects. This combination therapy includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexcd, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and episteride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge;

Biological response modifiers are agents that modify defense mechanisms of living organisms or biological responses such as survival, growth or differentiation of tissue cells to direct them to have anti-tumor activity; such agents include, e.g., krestin, lentinan, sizofuran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab;

EGFR (HER1) inhibitors such as, e.g., cetuximab, panitumumab, vectibix, gefitinib, erlotinib, and Zactima;

HER2 inhibitors such as, e.g., lapatinib, tratuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted antimitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors;

Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, aminoglutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

In a preferred embodiment, the compounds of the present invention may be used in combination with chemotherapy (i.e. cytotoxic agents), anti-hormones and/or targeted therapies such as other kinase inhibitors (for example, EGFR inhibitors), mTOR inhibitors and angiogenesis inhibitors.

The compounds of the present invention may also be employed in cancer treatment in conjunction with radiation therapy and/or surgical intervention.

Furthermore, the compounds of formula (I) may be utilized, as such or in compositions, in research and diagnostics, or as analytical reference standards, and the like, which are well known in the art.

Pharmaceutical Compositions and Methods of Treatment

In another aspect, the invention provides a pharmaceutical composition comprising a compound of formula (I) as defined above, together with a pharmaceutically acceptable carrier.

In still another aspect, the invention provides a process for preparing a pharmaceutical composition. The process includes the step of comprising combining at least one compound of formula (I) as defined above with at least one pharmaceutically acceptable carrier, and bringing the resulting combination into a suitable administration form.

The active component of formula (I) can act systemically and/or locally. For this purpose, it can be applied in a suitable manner, for example orally, parenterally, pulmonally, nasally, sublingually, lingually, buccally, rectally, transdermally, conjunctivally, otically, or as an implant or stent.

For these application routes, the active component of formula (I) can be administered in suitable application forms.

Useful oral application forms include application forms which release the active component rapidly and/or in modified form, such as, for example, tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include, for example, inhalatory pharmaceutical forms (including powder inhalers, nebulizers), nasal drops, solutions or sprays, tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders, implants or stents.

In a preferred embodiment, the pharmaceutical composition comprising a compound of formula (I) as defined above is provided in a form suitable for oral administration. In another preferred embodiment, the pharmaceutical composition comprising a compound of formula (I) as defined above is provided in a form suitable for intravenous administration.

The active component of formula (I) can be converted into the recited application forms in a manner known per se. This is carried out using inert non-toxic, pharmaceutically suitable excipients. These include, inter alia, carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

In another embodiment, the invention provides a method of treating a cell proliferative disorder in a patient in need of such treatment, comprising administering to the patient an effective amount of a compound of formula (I) as defined above. In certain embodiments, the cell proliferative disorder is cancer.

In still another aspect, the invention provides use of a compound of formula (I) as defined above for manufacturing a pharmaceutical composition for the treatment or prevention of a cell proliferative disorder. In certain embodiments, the cell proliferative disorder is cancer.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compounds of the invention, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.01 to 100 mg/kg per day or 0.1 to 150 mg/kg per day.

In certain embodiments, the compound of the invention can be used in combination therapy with conventional cancer chemotherapeutics. Conventional treatment regimens for leukemia and for other tumors include radiation, drugs, or a combination of both.

Determination of a therapeutically effective anti-proliferative amount or a prophylactically effective anti-proliferative amount of the compounds of the invention can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other coadministered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective anti-proliferative amount and a prophylactically effective anti-proliferative amount of a compound of the invention may be expected to vary from about 0.01 milligram per kilogram of body weight per day (mg/kg/day) to about 100 mg/kg/day.

A preferred dose of the compound of the invention for the present invention is the maximum that a patient can tolerate and not develop serious side effects. Illustratively, the compound of the present invention is administered at a dose of about 0.01 mg/kg to about 100 mg/kg of body weight, about 0.01 mg/kg to about 10 mg/kg of body weight or about 0.1 mg/kg to about 10 mg/kg of body weight. Ranges intermediate to the above-recited values are also intended to be part of the invention.

The percentages in the tests and examples which follows are, unless otherwise stated, by weight; parts are by weight. Solvent ratios, dilution ratios and concentrations reported for liquid/liquid solutions are each based on volume.

A. EXAMPLES

Abbreviations and Acronyms aq. aqueous (solution)
br. s broad singlet (NMR)
conc. concentrated
d doublet (NMR)
DCI direct chemical ionization (MS)
dd doublet of doublets (NMR)
DMF N,N-dimethylformamide
DMSO dimethylsulfoxide
DMSO-$d_6$ dimethylsulfoxide-$d_6$
ee enantiomeric excess
equiv. equivalent(s)
ESI electro-spray ionization (MS)
Et ethyl
EtOAc ethyl acetate
GC-MS gas chromatography-coupled mass spectrometry
h hour(s)
$^1$H-NMR proton nuclear magnetic resonance spectrometry
HOAc acetic acid
HPLC high performance/high pressure liquid chromatography
LC-MS liquid chromatography-coupled mass spectrometry
m multiplet (NMR)
Me methyl
MeOH methanol
min minute(s)
MS mass spectrometry
m/z mass-to-charge ratio
of th. of theory (chemical yield)
q quartet (NMR)
$R_f$ TLC retention factor
RP reverse phase (HPLC)
rt room temperature
$R_t$ retention time (HPLC)
s singlet (NMR)
tBu tert-butyl
tBuO tert-butoxy
TFA trifluoroacetic acid
THF tetrahydrofuran
TLC thin layer chromatography
t triplet (NMR)
v/v volume-to-volume ratio
w/v weight-to-volume ratio
w/w weight-to-weight ratio LC-MS and GC-MS Methods:

Method 1 (LC-MS):
Instrument: Micromass ZQ with HPLC Waters Alliance 2795; column: Phenomenex Synergi 2.5µ MAX-RP 100A Mercury, 20 mm×4 mm; eluent A: 1 L water+0.5 mL 50% formic acid, eluent B: 1 L acetonitrile+0.5 mL 50% formic acid; gradient: 0.0 min 90% A→0.1 min 90% A→3.0 min 5% A→4.0 min 5% A→4.01 min 90% A; flow rate: 2 mL/min; oven: 50° C.; UV detection: 210 nm.

Method 2 (LC-MS):
Instrument: Micromass Quattro Premier with HPLC Waters HPLC Acquity; column: Thermo Hypersil GOLD 1.9µ, 50 mm×1 mm; eluent A: 1 L water+0.5 mL 50% formic acid, eluent B: 1 L acetonitrile+0.5 mL 50% formic acid; gradient: 0.0 min 90% A→0.1 min 90% A→1.5 min 10% A→2.2 min 10% A; oven: 50° C.; flow rate: 0.33 mL/min; UV detection: 210 nm.

Method 3 (GC-MS):
Instrument: Micromass GCT, GC6890; column: Restek RTX-35, 15 m×200 µm×0.33 µm; constant flow with helium: 0.88 mL/min; oven: 70° C.; inlet: 250° C.; gradient: 70° C., 30° C./min→310° C. (keep for 3 min).

Method 4 (LC-MS):
Instrument: Waters Acquity SQD HPLC System; column: Waters Acquity HPLC HSS T3 1.8µ, 50 mm×1 mm; eluent A: 1 L water+0.25 mL 99% formic acid, eluent B: 1 L acetonitrile+0.25 mL 99% formic acid; gradient: 0.0 min 90% A→1.2 min 5% A→2.0 min 5% A; oven: 50° C.; flow rate: 0.40 mL/min; UV detection: 210-400 nm.

Method 5 (LC-MS):
Instrument: Micromass ZQ with HPLC HP 1100 Series; UV DAD; column: Phenomenex Gemini 3µ 30 mm×3.00 mm; eluent A: 1 L water+0.5 mL 50% formic acid, eluent B: 1 L acetonitrile+0.5 mL 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV-detection: 210 nm.

Starting Materials and Intermediates

Example 1A

3-Methyl-1H-indazole-5-carbaldehyde

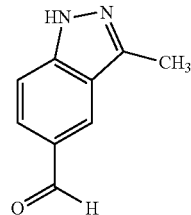

Tetrahydrofuran (600 ml) was cooled down to −78° C. under argon atmosphere. At this temperature, a 1.7 M solution of tert-butyllithium in n-pentane (200 ml) was added dropwise. After 15 minutes at −78° C., a solution of 22.4 g (106.1 mmol) 5-bromo-3-methyl-1H-indazole in THF (300 ml) was added dropwise at such a rate that the temperature of the solution did not exceed −70° C. The mixture was stirred for 30 minutes before N,N-dimethylformamide (24.5 ml) was added dropwise. After 20 min, the cooling bath was removed, and stirring was continued for 1 h before water (250 ml) was added carefully. The mixture was extracted several times with ethyl acetate (500 ml). The combined organic layers were washed with saturated aqueous sodium chloride solution, dried over sodium sulfate, and concentrated under reduced pressure to yield 18.5 g of crude 3-methyl-1H-indazole-5-carbaldehyde, which was used in the next step without further purification.

$^1$H-NMR (DMSO-d$_6$): δ=13.13 (br. s, 1H), 10.01 (s, 1H), 8.40 (s, 1H), 7.81 (d, 1H), 7.58 (d, 1H), 2.56 (s, 3H) ppm.

Example 2A (2E)-2-[(3-Methyl-1H-indazol-5-yl)methylidene]-3-oxobutanenitrile

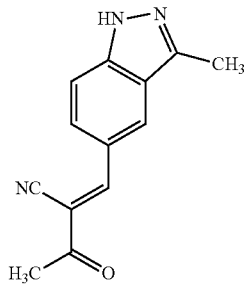 [SMILES: CC(=O)/C(C#N)=C/c1ccc2[nH]nc(C)c2c1]

A mixture of 5.0 g (31.2 mmol) 3-methyl-1H-indazole-5-carbaldehyde (Example 1A), 3.61 g (34.3 mmol) sodium (1Z)-1-cyanoprop-1-en-2-olate, 2.23 ml (39 mmol) acetic acid and 0.31 ml (3.12 mmol) piperidine in dry dichloromethane (250 ml) containing 4 Å molecular sieve was stirred under reflux for 12 h. Upon cooling, a precipitate was formed which was collected by filtration and washed with saturated aqueous sodium bicarbonate solution and water. The solid was dissolved in ethanol, and the molecular sieve was filtered off. The filtrate was concentrated under reduced pressure, and the residue was treated with ethyl acetate and saturated aqueous sodium carbonate solution. The organic layer was washed with water, dried, and concentrated under reduced pressure to afford the title compound (3.5 g, 50% of th.) as a pale yellow solid which was used in the next step without further purification.

LC-MS (method 1): R$_t$=1.32 min; MS (ESIpos): m/z=226 (M+H)$^+$ $^1$H-NMR (400 MHz, DMSO-d$_6$): δ=13.18 (br. s, 1H), 8.52 (s, 1H), 8.49 (s, 1H), 8.19 (d, 1H), 7.69 (d, 1H), 2.55 (br. m, 6H) ppm.

Example 3A

5-Methoxy-3,6-dihydro-2H-1,4-oxazine

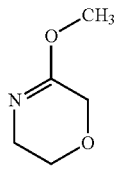

A solution of 1.2 g (11.9 mmol) morpholine-3-one in dichloromethane (70 ml) was cooled to 0° C. and treated with 25 g (238 mmol) dry sodium carbonate. After stirring for 10 min at 0° C., 6.14 g (41.5 mmol) trimethyloxonium tetrafluoroborate were added at 0° C. The mixture was allowed to warm to room temperature and stirred for 6 h. Water (100 ml) was added, and the organic layer was separated. The aqueous phase was extracted several times with dichloromethane, and the combined organic layers were washed with brine, dried over sodium sulfate and concentrated under reduced pressure. The crude product thus obtained was used in the next step without further purification.

GC-MS (method 3): R$_t$=3.36 min; MS (ESIpos): m/z=116 (M+H)$^+$.

Example 4A tert-Butyl (2E/Z)-cyano(morpholin-3-ylidene)ethanoate

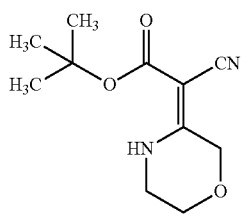 [SMILES: CC(C)(C)OC(=O)/C(C#N)=C1/COCCN1]

A mixture of 0.48 g (4.17 mmol) 5-methoxy-3,6-dihydro-2H-1,4-oxazine (Example 3A) and 0.61 g (4.34 mmol) tert-butyl cyanoacetate in THF (25 ml) was stirred under reflux for 12 h. The mixture was then cooled to room temperature and concentrated under reduced pressure. The residue was purified by flash chromatography (silica gel, eluent cyclohexane/ethyl acetate 3:1) to yield the title compound as a white solid (0.269 g, 27% of th.).

LC-MS (method 2): R$_t$=0.99 min; MS (ESIpos): m/z=225 (M+H)$^+$ $^1$H-NMR (400 MHz, DMSO-d$_6$): δ=10.02 (br. s, 1H), 4.47 (s, 2H), 3.84 (t, 2H), 3.37 (m, 2H), 1.44 (s, 9H) ppm.

Example 5A 1-(5-Bromo-2-fluorophenyl)-1-propanol

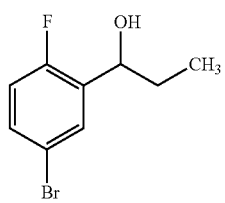

To a solution of 15 g (73.9 mmol) 5-bromo-2-fluorobenzaldehyde in diethyl ether (100 ml) at 0° C. were slowly added 27.1 ml (81.3 mmol) of ethyl magnesium bromide solution (3 M in diethyl ether). After stirring at 0° C. for 3 h, water (20 ml) was carefully added upon which a white precipitate formed. The solid was filtered off and washed with tert-butylmethyl ether. The combined filtrates were washed with brine, dried over sodium sulfate and concentrated under reduced pressure. The crude title compound thus obtained (16.1 g, 93% of th.) was used in the next step without further purification.

GC-MS (method 3): $R_t$=4.54 min; MS (EIpos): m/z=232 (M)$^+$.

Example 6A 1-(5-Bromo-2-fluorophenyl)-1-propanone

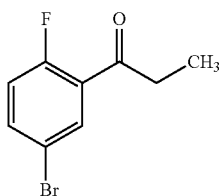

A mixture of 10 g (42.9 mmol) 1-(5-bromo-2-fluorophenyl)-1-propanol (Example 5A), 8.75 g (85.8 mmol) neutral aluminium oxide and 18.5 g (85.8 mmol) pyridinium chlorochromate in dichloromethane (100 ml) was stirred at room temperature for 4 h. The mixture was then filtered through silica gel (200 g, 0.06-0.2 mm) which was thoroughly washed with dichloromethane (1000 ml). The combined filtrates were washed with brine, dried over sodium sulfate and concentrated under reduced pressure. The crude title compound thus obtained (8.6 g, 87% of th.) was used in the next step without further purification.

GC-MS (method 3): $R_t$=4.30 min; MS (EIpos): m/z=230 (M)$^+$.

Example 7A

5-Bromo-3-ethyl-1H-indazole

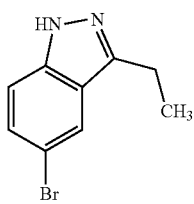

A solution of 7.50 g (32.5 mmol) 1-(5-bromo-2-fluorophenyl)-1-propanone (Example 6A) in 1-methyl-2-pyrrolidinone (NMP; 100 ml) was treated with 3.25 g (3.16 ml, 64.9 mmol) hydrazine hydrate and stirred at reflux temperature for 16 h. Upon cooling, the mixture was poured into a mixture of ice and water. The precipitate was collected by filtration and washed thoroughly with water to yield 4.56 g (62% of th.) of the title compound as a beige-coloured solid.

LC-MS (method 4): $R_t$=1.00 min; MS (ESIpos): m/z=225 (M+H)$^+$.

Example 8A

3-Ethyl-1H-indazole-5-carbaldehyde

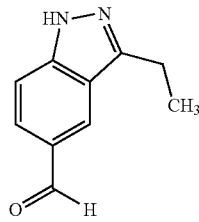

A solution of 6.90 g (30.7 mmol) 5-bromo-3-ethyl-1H-indazole (Example 7A) in THF (300 ml) was cooled to −78° C. At this temperature, a 1.7 M solution of tert-butyllithium in n-pentane (63.1 ml, 107 mmol) was slowly added. The mixture was stirred at −78° C. for 30 minutes before N,N-dimethylformamide (80.0 ml) was slowly added. The cooling bath was removed, and stirring was continued until room temperature was reached. Then, water (250 ml) was added carefully. The mixture was extracted several times with ethyl acetate (500 ml). The combined organic layers were washed with saturated aqueous sodium chloride solution, dried over sodium sulfate, and concentrated under reduced pressure to yield 4.5 g (84% of th.) of the crude title compound which was used in the next step without further purification.

LC-MS (method 4): $R_t$=0.73 min; MS (ESIpos): m/z=175 (M+H)$^+$.

Example 9A (2E)-2-[(3-Ethyl-1H-indazol-5-yl)methylidene]-3-oxobutanenitrile

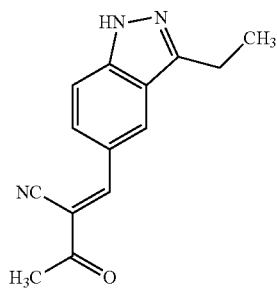 [SMILES: CCc1n[nH]c2ccc(/C=C(\C#N)C(C)=O)cc12]

A mixture of 0.50 g (2.87 mmol) 3-ethyl-1H-indazole-5-carbaldehyde (Example 8A), 0.33 g (3.16 mmol) sodium (1Z)-1-cyanoprop-1-en-2-olate, 0.21 ml (3.6 mmol) acetic acid and 0.028 ml (0.29 mmol) piperidine in dry dichloromethane (25 ml) containing 4 Å molecular sieve was stirred under reflux for 16 h. Upon cooling, a precipitate was formed which was collected by filtration and washed with saturated aqueous sodium bicarbonate solution and water. The solid was dissolved in ethanol, and the molecular sieve was filtered off. The filtrate was concentrated under reduced pressure, and the residue was treated with ethyl acetate and saturated aqueous sodium carbonate solution. The organic layer was washed with water, dried, and concentrated under reduced pressure to afford the title compound (0.60 g, 88% of th.) as a pale yellow solid which was used in subsequent steps without further purification.

LC-MS (method 1): $R_t$=1.50 min; MS (ESIpos): m/z=240 (M+H)$^+$ $^1$H-NMR (400 MHz, DMSO-d$_6$): δ=13.17 (br. s, 1H), 8.59 (s, 1H), 8.51 (s, 1H), 8.17 (d, 1H), 7.67 (d, 1H), 2.97 (q, 2H), 2.55 (br. m, 3H), 1.36 (t, 3H) ppm.

Example 10A

3-Bromo-1H-indazole-5-carbaldehyde

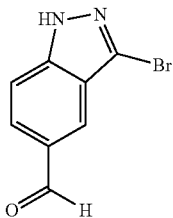 [SMILES: O=Cc1ccc2[nH]nc(Br)c2c1]

To a solution of 20 g (137 mmol) 1H-indazole-5-carbaldehyde in acetonitrile (580 ml), 28 g (157 mmol) 1-bromopyrrolidine-2,5-dione were added over 20 min at room temperature. The resulting suspension was stirred under reflux for 30 min, then cooled to room temperature and concentrated under reduced pressure. The residue was dissolved in ethyl acetate (1500 ml), and the solution was washed with water and with brine, dried over sodium sulfate, filtered and concentrated under reduced pressure. The crude product was triturated with ethyl acetate. After filtration, the precipitate was dried under vacuum to yield the title compound as a white solid (30.9 g, 75% of th.).

LC-MS (method 4): $R_t$=0.77 min; MS (ESIpos): m/z=225 (M+H)$^+$ $^1$H-NMR (400 MHz, DMSO-d$_6$): δ=15.01 (br. s, 1H), 10.09 (s, 1H), 8.29 (s, 1H), 7.91 (d, 1H), 7.73 (d, 1H) ppm.

Example 11A (2E)-2-[(3-Bromo-1H-indazol-5-yl)methylidene]-3-oxobutanenitrile

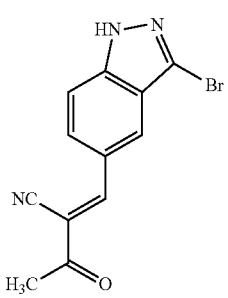

The title compound was prepared from 2.85 g (70% purity, 8.87 mmol) 3-bromo-1H-indazole-5-carbaldehyde (Example 10A) and 1.03 g (9.75 mmol) sodium (1Z)-1-cyanoprop-1-en-2-olate in analogy to the procedure described in Example 9A yielding 1.12 g (43% of th.) of product which was used in subsequent steps without further purification.

LC-MS (method 4): $R_t$=0.89 min; MS (ESIpos): m/z=291 (M+H)$^+$ $^1$H-NMR (400 MHz, DMSO-d$_6$): δ=13.55 (br. s, 1H), 8.75 (d, 1H), 8.42 (s, 1H), 8.38 (s, 1H), 7.58 (d, 1H), 2.5 (br. s, 3H) ppm.

Example 12A 8-(3-Bromo-1H-indazol-5-yl)-6-methyl-1,3,4,8-tetrahydropyrido[2,1-c][1,4]oxazine-7,9-dicarbonitrile

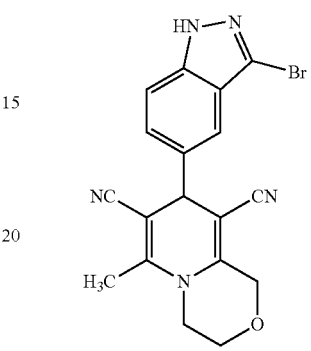

The title compound was prepared from 518 mg (1.78 mmol) (2E)-2-[(3-bromo-1H-indazol-5-yl)-methylidene]-3-oxobutanenitrile (Example 11A) and 400 mg (1.78 mmol) tert-butyl (2E/Z)-cyano-(morpholin-3-ylidene)ethanoate (Example 4A) in analogy to the procedure described in Example 1 yielding 264 mg (88% purity, 37% of th.) of product after flash-chromatography (silica gel; eluent toluene/ethanol 20:1 v/v). This material could be used in the next step without further purification.

A batch of 140 mg was re-purified by preparative RP-HPLC (acetonitrile/water gradient) to yield 61 mg of the pure title compound as a white solid.

LC-MS (method 2): $R_t$=1.00 min; MS (ESIpos): m/z=396 (M+H)$^+$ $^1$H-NMR (400 MHz, DMSO-d$_6$): δ=13.51 (s, 1H), 7.64 (d, 1H), 7.49 (d, 1H), 7.48 (s, 1H), 4.68 (s, 1H), 4.53 (m, 2H), 3.95 (m, 2H), 3.65 (m, 2H), 2.25 (s, 3H) ppm.

Example 13A

6-Fluoro-1H-indazole-5-carbaldehyde

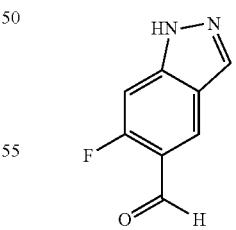

A slurry of 4.8 g (30 mmol) 6-fluoro-1H-indazole-5-carbonitrile [commercially available; preparation given in EP 1 510 516-A1 (production example 82)] in anhydrous toluene (150 ml) was cooled to −40° C. Under inert gas atmosphere, 48 ml (72 mmol) diisobutylaluminium hydride solution (1.5 M in toluene) were added over 30 min, and the resulting mixture was stirred at −40° C. for 3 h. Then, ethyl acetate (30 ml) was added, and the mixture was stirred for further 20 min at −40° C. followed by dropwise addition of aqueous tartaric acid (1 M, 30 ml). The mixture was allowed to warm to 0° C. and filtered at this temperature. The filtrate was extracted with ethyl acetate several times, and the combined organic phases were subsequently washed with saturated aqueous sodium hydrogencarbonate and with brine, dried over sodium sulfate, filtered and concentrated under reduced pressure. The crude product thus obtained (2.60 g, 53% of th.) was used in the next step without further purification.

LC-MS (method 4): $R_t$=0.59 min; MS (ESIpos): m/z=165 (M+H)$^+$.

Example 14A (2E)-2-[(6-Fluoro-1H-indazol-5-yl)methylidene]-3-oxobutanenitrile

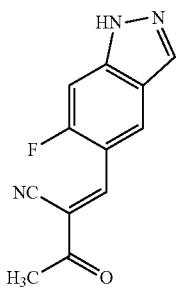 [SMILES: CC(=O)/C(C#N)=C/c1cc2cn[nH]c2cc1F]

The title compound was prepared from 3.7 g (80% purity, 18.0 mmol) 6-fluoro-1H-indazole-5-carbaldehyde (Example 13A) and 2.08 g (19.84 mmol) sodium (1Z)-1-cyanoprop-1-en-2-olate in analogy to the procedure described in Example 9A yielding 2.5 g (61% of th.) of product which was used in subsequent steps without further purification.

LC-MS (method 2): $R_t$=0.71 min; MS (ESIpos): m/z=230 (M+H)$^+$ $^1$H-NMR (400 MHz, DMSO-d$_6$): δ=13.90 (s, 1H), 8.59 (s, 1H), 8.46 (s, 1H), 8.23 (d, 1H), 7.80 (d, 1H), 2.5 (br. s, 3H) ppm.

Example 15A 8-(6-Fluoro-1H-indazol-5-yl)-6-methyl-1,3,4,8-tetrahydropyrido[2,1-c][1,4]oxazine-7,9-dicarbonitrile

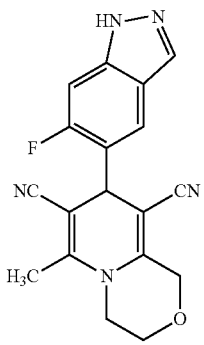 [SMILES: CC1=C(C#N)C(c2cc3cn[nH]c3cc2F)C(C#N)=C2COCCN12]

The title compound was prepared from 97 mg (0.422 mmol) (2E)-2-[(6-fluoro-1H-indazol-5-yl)-methylidene]-3-oxobutanenitrile (Example 14A) and 95 mg (0.422 mmol) tert-butyl (2E/Z)-cyano-(morpholin-3-ylidene)ethanoate (Example 4A) in analogy to the procedure described in Example 1 yielding 18 mg (12% of th.) of product.

LC-MS (method 4): $R_t$=0.80 min; MS (ESIpos): m/z=336 (M+H)$^+$ $^1$H-NMR (400 MHz, DMSO-d$_6$): δ=13.21 (s, 1H), 8.13 (s, 1H), 7.80 (d, 1H), 7.39 (d, 1H), 4.80 (s, 1H), 4.53 (m, 2H), 4.05-3.85 (m, 2H), 3.65 (m, 2H), 2.25 (s, 3H) ppm.

Preparation Examples

Example 1

6-Methyl-8-(3-methyl-1H-indazol-5-yl)-1,3,4,8-tetrahydropyrido[2,1-c][1,4]oxazine-7,9-dicarbonitrile

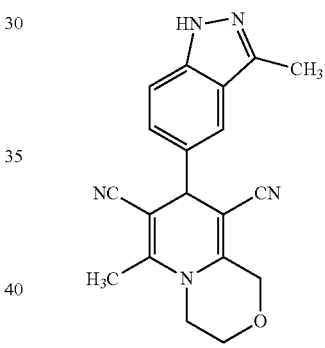

A mixture of 190 mg (0.84 mmol) tert-butyl (2E/Z)-cyano(morpholin-3-ylidene)ethanoate (Example 4A) in 6 M hydrochloric acid (10 ml) was heated to 100° C. for 15 min. After cooling to room temperature, the solution was concentrated under reduced pressure, and the remaining solid was dissolved in acetic acid (10 ml) at room temperature. 200 mg (0.88 mmol) (2E)-2-[(3-methyl-1H-indazol-5-yl)methylidene]-3-oxobutanenitrile (Example 2A) were added, and the mixture was stirred at 100° C. for 15 min. After cooling to room temperature, the mixture was concentrated under reduced pressure, and the residue was purified by flash chromatography (silica gel; eluent ethyl acetate/cyclohexane gradient, final mixture 1:1 v/v) followed by preparative RP-HPLC (acetonitrile/water gradient) to yield 18 mg (6% of th.) of the racemic title compound.

LC-MS (method 2): $R_t$=0.90 min; MS (ESIpos): m/z=332 (M+H)$^+$ $^1$H-NMR (400 MHz, DMSO-d$_6$): δ=12.69 (s, 1H), 7.56 (s, 1H), 7.50 (d, 1H), 7.32 (d, 1H), 4.6-4.45 (m, 3H), 4.03-3.86 (m, 2H), 3.64 (t, 2H), 3.32 (s, 3H), 2.24 (s, 3H) ppm.

Example 2 and Example 3

6-Methyl-8-(3-methyl-1H-indazol-5-yl)-1,3,4,8-tetrahydropyrido[2,1-c][1,4]oxazine-7,9-dicarbonitrile (Enantiomer 1 and 2)

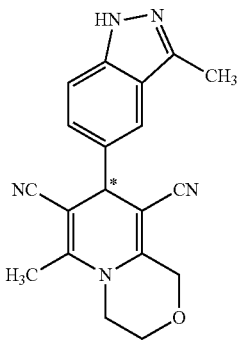

The racemic compound from Example 1 (190 mg) was separated into the enantiomers by HPLC chromatography on a chiral phase [column: Daicel Chiralpak AD-H, 5 μm, 250 mm×20 mm; eluent: isohexane/isopropanol 70:30 v/v; flow rate: 20 ml/min; temperature: 25° C.; UV detection: 230 nm]:

Example 2

Enantiomer 1

Yield: 11 mg (>99% ee)
$R_t$=7.40 min [column: Daicel Chiralpak AD-H, 5 μm, 250 mm×4 mm; eluent: isohexane/isopropanol 60:40 v/v; flow rate: 1 ml/min; temperature: 30° C.; UV detection: 230 nm].

Example 3

Enantiomer 2

Yield: 14 mg (96% ee)
$R_t$=8.59 min [column: Daicel Chiralpak AD-H, 5 μm, 250 mm×4 mm; eluent: isohexane/isopropanol 60:40 v/v; flow rate: 1 ml/min; temperature: 30° C.; UV detection: 230 nm].

Example 4

8-(3-Ethyl-1H-indazol-5-yl)-6-methyl-1,3,4,8-tetrahydropyrido[2,1-c][1,4]oxazine-7,9-dicarbonitrile

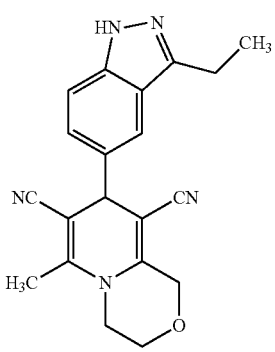 [SMILES: CCc1n[nH]c2ccc(C3C(C#N)=C(C)N4CCOCC4=C3C#N)cc12]

The title compound was prepared from 139 mg (0.58 mmol) (2E)-2-[(3-ethyl-1H-indazol-5-yl)-methylidene]-3-oxobutanenitrile (Example 9A) and 130 mg (0.58 mmol) tert-butyl (2E/Z)-cyano-(morpholin-3-ylidene)ethanoate (Example 4A) in analogy to the procedure described in Example 1 yielding 180 mg (90% of th.) of the racemic product.

LC-MS (method 5): $R_t$=1.86 min; MS (ESIpos): m/z=346 (M+H)$^+$ $^1$H-NMR (400 MHz, DMSO-d$_6$): δ=12.69 (s, 1H), 7.58 (s, 1H), 7.51 (d, 1H), 7.33 (d, 1H), 4.55 (s, 1H), 4.52 (m, 2H), 4.05-3.85 (m, 2H), 3.64 (m, 2H), 2.94 (q, 2H), 2.32 (s, 3H), 1.32 (t, 3H) ppm.

Example 5 and Example 6

8-(3-Ethyl-1H-indazol-5-yl)-6-methyl-1,3,4,8-tetrahydropyrido[2,1-c][1,4]oxazine-7,9-dicarbonitrile (Enantiomer 1 and 2)

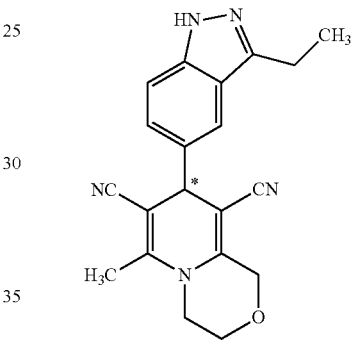

The racemic compound from Example 4 (150 mg) was separated into the enantiomers by HPLC chromatography on a chiral phase [column: Daicel Chiralpak AD-H, 5 μm, 250 mm×20 mm; eluent: isohexane/isopropanol 70:30 v/v; flow rate: 20 ml/min; temperature: 25° C.; UV detection: 230 nm]:

Example 5

Enantiomer 1

Yield: 28 mg (>99% ee)
$R_t$=6.19 min [column: Daicel Chiralpak AD-H, 5 μm, 250 mm×4 mm; eluent: isohexane/isopropanol 60:40 v/v; flow rate: 1 ml/min; temperature: 30° C.; UV detection: 230 nm].

Example 6

Enantiomer 2

Yield: 50 mg (94% ee)
$R_t$=6.92 min [column: Daicel Chiralpak AD-H, 5 μm, 250 mm×4 mm; eluent: isohexane/isopropanol 60:40 v/v; flow rate: 1 ml/min; temperature: 30° C.; UV detection: 230 nm].

Example 7

8-[3-(6-Fluoropyridin-3-yl)-1H-indazol-5-yl]-6-methyl-1,3,4,8-tetrahydropyrido[2,1-c][1,4]-oxazine-7,9-dicarbonitrile

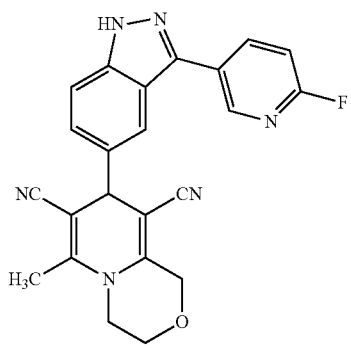 [SMILES: CC1=C(C#N)C(c2ccc3[nH]nc(-c4ccc(F)nc4)c3c2)C(C#N)=C2COCCN12]

To a degassed solution of 125 mg (0.315 mmol) 8-(3-bromo-1H-indazol-5-yl)-6-methyl-1,3,4,8-tetrahydropyrido[2,1-c][1,4]oxazine-7,9-dicarbonitrile (Example 12A) and 53.3 mg (0.379 mmol) (6-fluoropyridin-3-yl)boronic acid in anhydrous 1,4-dioxane (2.2 ml) were added under inert gas atmosphere 36.5 mg (0.032 mmol) tetrakis(triphenylphosphine)palladium(0) and aqueous sodium bicarbonate solution (2 M, 0.56 ml). The resulting mixture was stirred at 140° C. for 70 min under microwave conditions. After cooling to room temperature and concentration under reduced pressure, the remaining solid was dissolved in ethyl acetate (20 ml). The solution was subsequently washed with water and with brine, dried over sodium sulfate and concentrated under reduced pressure. The crude product was purified by preparative RP-HPLC (acetonitrile/water gradient, final mixture 95:5 v/v) to yield the title compound as a white solid (64 mg, 49% of th.).

LC-MS (method 4): $R_t$=0.90 min; MS (ESIpos): m/z=413 (M+H)$^+$ $^1$H-NMR (400 MHz, DMSO-$d_6$): δ=13.54 (s, 1H), 8.82 (s, 1H), 8.54 (m, 1H), 8.00 (s, 1H), 7.69 (d, 1H), 7.48 (d, 1H), 7.48 (m, 1H), 4.68 (s, 1H), 4.53 (m, 2H), 3.95 (m, 2H), 3.65 (m, 2H), 2.25 (s, 3H) ppm.

B. EVALUATION OF BIOLOGICAL ACTIVITY

Demonstration of the activity of the compounds of the present invention may be accomplished through in vitro, ex vivo, and in vivo assays that are well known in the art. For example, to demonstrate the activity of the compounds of the present invention, the following assays may be used.

c-Met Receptor Tyrosine Kinase Activity Assay (NADH Read-Out):

Recombinant human c-Met protein (Invitrogen, Carlsbad, Calif., USA) is used. As substrate for the kinase reaction the peptide KKKSPGEYVNIEFG (JPT, Germany) is used. For the assay, 1 µL of a 51-fold concentrated solution of the test compound in DMSO is pipetted into a white 384-well microtiter plate (Greiner Bio-One, Frickenhausen, Germany). 25 µL of a solution of c-Met (final concentration 30 nM) and pyruvate kinase/lactate dehydrogenase (Roche Diagnostics, Mannheim, Germany; final concentration 8 mg/L) in assay buffer [3-(N-morpholino)propane-sulfonic acid (MOPS), 50 mM, pH 7; MgCl$_2$, 10 mM; bovine serum albumin (BSA), 0.01%; Triton X 100, 0.01%; DTT, 2 mM] are added, and the mixture is incubated for 5 min at room temperature. Then, the kinase reaction is started by the addition of 25 µL of a solution of adenosine triphosphate (ATP, final concentration 30 µM), substrate (final concentration 100 µM), nicotinamide adenine dinucleotide (NADH, final concentration 50 µM) and dithiothreitol (DTT, final concentration 2 mM) in assay buffer, and the resulting mixture is incubated for a reaction time of 100 min at 32° C.

Subsequently, the amount of phosphorylated substrate is evaluated by measurement of the decrease of NADH fluorescence. Therefore, the fluorescence emissions at 465 nm after excitation at 340 nm is measured in a fluorescence reader, e.g. Tecan Ultra (Tecan, Männedorf, Switzerland). The data are normalised (enzyme reaction without inhibitor=0% inhibition; all other assay components but no enzyme=100% inhibition). Normally, test compounds are tested on the same microtiter plate at 9 different concentrations in the range of 10 µM to 1 nM (10 µM, 3.1 µM, 1.0 µM, 0.3 µM, 0.1 µM, 0.03 µM, 0.01 µM, 0.003 µM, 0.001 µM; dilution series prepared before the assay at the level of the 51-fold concentrated stock solutions by serial 1:3 dilutions) in duplicate for each concentration, and IC$_{50}$ values are calculated using an inhouse software.

Compounds of the invention, when tested in this assay, demonstrated the ability to inhibit c-Met tyrosine kinase activity at IC$_{50}$ values of less than 10 µM, preferably at less than 1 µM.

Some representative IC$_{50}$ values are listed in the table below:

| Example No. | IC$_{50}$ [µM] |
|---|---|
| 2 | 0.008 |
| 5 | 0.012 |
| 6 | 0.088 |
| 7 | 0.023 | c-Met Receptor Tyrosine Kinase Homogeneous Time-Resolved Fluorescence Assay (Alternative Format):

The N-terminally His6-tagged recombinant kinase domain of the human c-Met (amino acids 960-1390), expressed in insect cells (SF21) and purified by Ni-NTA affinity chromatography and consecutive size exclusion chromatography (Superdex 200), is used. Alternatively, commercially available c-Met (Millipore) can be used. As substrate for the kinase reaction, the biotinylated poly-Glu,Tyr (4:1) copolymer (#61GT0BLC, Cis Biointernational, Marcoule, France) is used.

For the assay, 50 nL of a 100-fold concentrated solution of the test compound in DMSO is pipetted into a black low-volume 384-well microtiter plate (Greiner Bio-One, Frickenhausen, Germany). 2 µL of a solution of c-Met in assay buffer [25 mM Hepes/NaOH, pH 7.5; 5 mM MgCl$_2$; 5 mM MnCl$_2$; 2 mM dithiothreitol; 0.1% (v/v) Tween 20 (Sigma); 0.1% (w/v) bovine serum albumin] are added, and the mixture is incubated for 15 min at 22° C. to allow pre-binding of the test compound to the enzyme before the start of the kinase reaction. Then, the kinase reaction is started by the addition of 3 µL of a solution of adenosine triphosphate (ATP, 16.7 µM; final concentration in the 5 µL assay volume is 10 µM) and substrate (2.27 µg/mL, final concentration in the 5 µL assay volume is 1.36 µg/mL~30 nM) in assay buffer, and the resulting mixture is incubated for a reaction time of 30 min at 22° C. The concentration of c-Met in the assay is adjusted depending on the activity of the enzyme lot and is appropriately chosen to have the assay in the linear range; typical enzyme concentrations are in the range of about 0.03 nM (final concentration in the 5 µL assay volume). The reaction is stopped by the addition of 5 µL of a solution of HTRF detection reagents [40 nM streptavidine-XLent and 2.4 nM PT66-Eu-chelate, an europium-chelate labelled anti-phosphotyrosine antibody (Perkin-Elmer)] in an aqueous EDTA solution [100 mM EDTA, 0.2% (w/v) bovine serum albumin in 50 mM HEPES/NaOH, pH 7.5].

The resulting mixture is incubated for 1 h at 22° C. to allow the binding of the biotinylated phosphorylated peptide to the streptavidine-XLent and the PT66-Eu-chelate. Subsequently, the amount of phosphorylated substrate is evaluated by measurement of the resonance energy transfer from the PT66-Eu-chelate to the streptavidine-XLent. Therefore, the fluorescence emissions at 620 nm and 665 nm after excitation at 350 nm are measured in an HTRF reader, e.g. Rubystar (BMG Lab-technologies, Offenburg, Germany) or Viewlux (Perkin-Elmer). The ratio of the emissions at 665 nm and at 622 nm is taken as the measure for the amount of phosphorylated substrate. The data are normalised (enzyme reaction without inhibitor=0% inhibition; all other assay components but no enzyme=100% inhibition). Normally, test compounds are tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM; dilution series prepared before the assay at the level of the 100-fold concentrated stock solutions by serial 1:3 dilutions) in duplicate for each concentration, and $IC_{50}$ values are calculated by a 4-parameter-fit using an inhouse software.

Compounds of the invention, when tested in this assay, demonstrated the ability to inhibit c-Met tyrosine kinase activity at $IC_{50}$ values of less than 10 µM, preferably at less than 1 µM.

Some representative $IC_{50}$ values are listed in the table below:

| Example No. | $IC_{50}$ [µM] |
|---|---|
| 2 | 0.001 |
| 4 | 0.023 |
| 7 | 0.002 |

Phospho-c-Met Assay:

This is a cell based, ELISA-like assay [Meso Scale Discovery (MSD), Gaithersburg, Md., USA] using MKN-45 tumor cells (gastric carcinoma, purchased from ATCC) without growth factor stimulation. The cells are plated in full growth media (10 000 cells/well) in 96-well plates on day one. On day two, after a two-hour drug treatment in serum-free media, cells are washed and then lysed (60 µl/well using MSD recommended lysis buffer) and frozen at −80° C. Also on day two, non-specific antibody-binding sites on the MSD phospho-Met plates are blocked with MSD Blocking Solution A overnight at 4° C. On day three, frozen lysates are thawed on ice, and 25 µl of lysate is transferred to the MSD phospho-Met plate, for 1 hour with shaking, after washing once with Tris-buffered saline+0.05% Tween 20 (TBST). After removing the unbound proteins, the Sulfa-TAG anti-Met antibody from MSD is added at a final concentration of 5 nM in antibody dilution buffer (following protocol of MSD) to the plate for 1 hour with shaking. The plate is then washed with TBST buffer three times before adding 1×MSD Read Buffer. The plate is then read on the MSD Discovery Workstation instrument. Raw data, including wells with 10 µM of a reference compound (minimum signal), and DMSO wells without any drug treatment (maximum signal), are entered into the Analyze 5 program for $IC_{50}$ value determinations.

Cellular Phospho-c-Met Assay:

Human gastric adenocarcinoma cells (MKN45, purchased from ATCC) seeded on 384-well microtiter plates (9000 cells/well) are incubated in 25 µl full growth media for 24 h at 37° C. with 5% $CO_2$. On day two, after a two-hour drug treatment in serum-reduced media containing 0.1% FCS, cells are washed and lysed. Lysates are transferred to BSA-blocked plates with prebound c-Met capture antibody [purchased from Mesoscale Discovery (MSD), Gaithersburg, Md., USA] for 1 hour with shaking, after washing once with Tris-buffered saline+0.05% Tween 20 (TBST). Following the MSD protocol, the Sulfa-TAG anti-phospho-c-Met detection antibody is added at a final concentration of 5 nM in antibody dilution buffer to the plate for 1 hour with shaking at RT. After washing the wells with Tris buffer, 1× reading buffer is added, and the plates are measured on the Sector Imager 6000 (purchased from Mesoscale). $IC_{50}$ values are calculated from dose-response curves using Marquardt-Levenberg-Fit.

In-Vitro Tumor Cell Proliferation Assay:

The adherent tumor cell proliferation assay used to test the compounds of the present invention involves a read-out called Cell Titre-Glo developed by Promega [B. A. Cunningham, "A Growing Issue: Cell Proliferation Assays. Modern kits ease quantification of cell growth", *The Scientist* 2001, 15 (13), 26; S. P. Crouch et al., "The use of ATP bioluminescence as a measure of cell proliferation and cytotoxicity", *Journal of Immunological Methods* 1993, 160, 81-88]. Generation of a luminescent signal corresponds to the amount of ATP present, which is directly proportional to the number of metabolically active (proliferating) cells.

H460 cells (lung carcinoma, purchased from ATCC) are plated in 96-well plates at 3000 cells/well in complete media with 10% fetal calf serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titre-Glo Luminescent® assay kit, the cells are lysed, and 100 µl of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of $IC_{50}$ values, a linear regression analysis can be used to determine the drug concentration which results in a 50% inhibition of cell proliferation using this assay format. This protocol can be applied to different cell lines of interest, which include, but not limited to, CAKI-1, MNK-45, GTL-16, HCC2998, K562, H441, K812, MEG01, SUP15 and HCT116.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

C. EXAMPLES RELATING TO PHARMACEUTICAL COMPOSITIONS

Pharmaceutical compositions according to the present invention can be illustrated as follows:

Sterile I.V. Solution:

A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilized Powder for I.V. Administration:

A sterile preparation can be prepared with (i) 100-1000 mg of the desired compound of this invention as a lyophilized powder, (ii) 32-327 mg/ml sodium citrate, and (iii) 300-3000 mg Dextran 40. The formulation is reconstituted with sterile, injectable saline or 5% dextrose to a concentration of 10 to 20 mg/ml, which is further diluted with saline or 5% dextrose to 0.2 to 0.4 mg/ml, and is administered either as i.v. bolus or by i.v. infusion over 15-60 minutes.

Intramuscular Suspension:

The following solution or suspension can be prepared for intramuscular injection:

50 mg/ml of the desired, water-insoluble compound of this invention; 5 mg/ml sodium carboxymethylcellulose; 4 mg/mL TWEEN 80; 9 mg/ml sodium chloride; 9 mg/ml benzyl alcohol.

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water-miscible medicine mix.

Tablets:

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability, or delay absorption.

We claim:

1. A compound of formula (I)

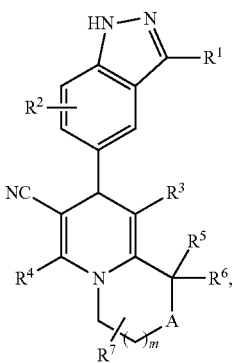

(I)

wherein
$R^1$ is selected from the group consisting of $(C_1-C_6)$-alkyl, $(C_3-C_7)$-cycloalkyl, phenyl, 4- to 7-membered heterocycloalkyl and 5- to 10-membered heteroaryl, wherein
(i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl,
and
(ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl,
wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^1$ is a group of the formula —$NR^8R^9$, —$C(\!=\!O)$—$NR^{10}R^{11}$, —$SO_2$—$NR^{12}R^{13}$, —$NR^{14}$—$C(\!=\!O)$—$R^{15}$, —$NR^{16}$—$SO_2$—$R^{17}$, —$OR^{18}$ or —$S(\!=\!O)_n$—$R^{19}$,
wherein
n is 0, 1 or 2,
$R^8, R^9, R^{10}, R^{11}, R^{12}$ and $R^{13}$ are independently selected from the group consisting of hydrogen, $(C_1-C_6)$-alkyl, $(C_3-C_7)$-cycloalkyl, phenyl, 4- to 7-membered heterocycloalkyl and 5- to 10-membered heteroaryl, wherein
(i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl,
and
(ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl,
wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^8$ and $R^9$, $R^{10}$ and $R^{11}$, $R^{12}$ and $R^{13}$ in pairs are joined and, taken together with the nitrogen atom to which each pair is attached, form a 4- to 7-membered heterocycloalkyl ring, which may contain a second ring heteroatom selected from N, O and S, and which is optionally substituted with one or two substituents independently selected from the group consisting of fluoro, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl, $R^{14}$ and $R^{16}$ are hydrogen or $(C_1-C_6)$-alkyl, $R^{15}$, $R^{17}$, $R^{18}$ and $R^{19}$ are each selected from the group consisting of $(C_1-C_6)$-alkyl, $(C_3-C_7)$-cycloalkyl, phenyl, 4- to 7-membered heterocycloalkyl and 5- to 10-membered heteroaryl, wherein (i) said $(C_3-C_7)$-cycloalkyl, phenyl, 4- to 7-membered heterocycloalkyl and 5- to 10-membered heteroaryl are optionally substituted with one or two substituents independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, and (ii) said $(C_1-C_6)$-alkyl is optionally substituted with one, two or three substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_7)$-cycloalkyl, phenyl, 4- to 7-membered heterocycloalkyl and 5- to 10-membered heteroaryl, wherein said $(C_3-C_7)$-cycloalkyl, phenyl, 4- to 7-membered heterocycloalkyl and 5- to 10-membered heteroaryl substituents in turn are optionally substituted with one or two residues independently selected from the group consisting of fluoro, chloro, bromo, difluoromethyl, trifluoromethyl, $(C_1-C_4)$-alkyl, oxo, hydroxy, difluoromethoxy, trifluoromethoxy, $(C_1-C_4)$-alkoxy, amino, mono-$(C_1-C_4)$-alkylamino, di-$(C_1-C_4)$-alkylamino and $(C_3-C_6)$-cycloalkyl, or $R^{16}$ and $R^{17}$ are joined and, taken together with the nitrogen atom and $SO_2$ group to which they are attached, form a heterocyclic moiety of the formula

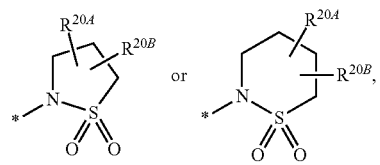

wherein * denotes the point of attachment to the indazole moiety, and $R^{20A}$ and $R^{20B}$ are independently selected from the group consisting of hydrogen, fluoro and $(C_1-C_4)$-alkyl, $R^2$ is hydrogen, fluoro, chloro or methyl, $R^3$ is cyano or a group of the formula $-C(=O)-OR^{21}$ or $-C(=O)-NR^{22}R^{23}$, wherein $R^{21}$ is $(C_1-C_6)$-alkyl optionally substituted with $(C_3-C_7)$-cycloalkyl, or is $(C_4-C_7)$-cycloalkyl, and $R^{22}$ and $R^{23}$ are independently selected from the group consisting of hydrogen, $(C_1-C_6)$-alkyl and $(C_3-C_7)$-cycloalkyl, wherein said $(C_1-C_6)$-alkyl is optionally substituted with $(C_3-C_7)$-cycloalkyl, $R^4$ is $(C_1-C_4)$-alkyl optionally substituted with up to three fluoro atoms, or is cyclopropyl or amino, $R^5$ is hydrogen, $(C_1-C_6)$-alkyl or $(C_3-C_7)$-cycloalkyl, wherein said $(C_1-C_6)$-alkyl is optionally substituted with up to three fluoro atoms or with one or two substituents independently selected from the group consisting of hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocycloalkyl, $R^6$ and $R^7$ are independently hydrogen or $(C_1-C_4)$-alkyl, and either (a)

A is O, S, S(=O) or S(=O)$_2$ and m is 1 or 2, or (b)

A is N($R^{24}$), wherein $R^{24}$ is hydrogen, $(C_1-C_6)$-alkyl, $(C_3-C_7)$-cycloalkyl or $(C_1-C_6)$-alkylcarbonyl, wherein said $(C_1-C_6)$-alkyl, $(C_3-C_7)$-cycloalkyl and $(C_1-C_6)$-alkylcarbonyl are optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino, and m is 1 or 2, in which case $R^5$ and $R^6$, in addition to the meanings specified above, may also be taken together and form an oxo group, or (c)

A is $-C(=O)-N(R^{25})-**$, wherein

** denotes the point of attachment to the $CR^5R^6$ group, and $R^{25}$ is hydrogen, $(C_1-C_6)$-alkyl or $(C_3-C_7)$-cycloalkyl, wherein said $(C_1-C_6)$-alkyl and $(C_3-C_7)$-cycloalkyl are optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino, and m is 0 or 1, or a hydrate, solvate, salt, or a hydrate or solvate of a salt thereof.

2. The compound of formula (I) according to claim 1, wherein
$R^1$ is selected from the group consisting of $(C_1-C_6)$-alkyl, $(C_3-C_6)$-cycloalkyl, phenyl, 4- to 6-membered heterocycloalkyl and 5- or 6-membered heteroaryl, wherein
  (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino, di-$(C_1-C_4)$-alkylamino and $(C_3-C_6)$-cycloalkyl,
  and
  (ii) said $(C_1-C_6)$-alkyl is optionally substituted with one or two substituents independently selected from the group consisting of hydroxy, $(C_1-C_4)$-alkoxy, amino, mono-$(C_1-C_4)$-alkylamino, di-$(C_1-C_4)$-alkylamino, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl,
    wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
or
$R^1$ is a group of the formula —$NR^8R^9$, —$C(=O)$—$NR^{10}R^{11}$, —$SO_2$—$NR^{12}R^{13}$, —$NR^{14}$—$C(=O)$—$R^{15}$, —$NR^{16}$—$SO_2$—$R^{17}$, —$OR^{18}$ or —$S(=O)_n$—$R^{19}$, wherein
  n is 0 or 2,
  $R^8$, $R^{10}$ and $R^{12}$ are each hydrogen or $(C_1-C_4)$-alkyl which is optionally substituted with one or two substituents independently selected from the group consisting of hydroxy, $(C_1-C_4)$-alkoxy, amino, mono-$(C_1-C_4)$-alkylamino and di-$(C_1-C_4)$-alkylamino,
  $R^9$, $R^{11}$ and $R^{13}$ are each selected from the group consisting of hydrogen, $(C_1-C_6)$-alkyl, $(C_3-C_6)$-cycloalkyl, phenyl, 4- to 6-membered heterocycloalkyl and 5- or 6-membered heteroaryl, wherein
    (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
    and
    (ii) said $(C_1-C_6)$-alkyl is optionally substituted with one or two substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl,
      wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
or
$R^8$ and $R^9$, $R^{10}$ and $R^{11}$, $R^{12}$ and $R^{13}$ in pairs are joined and, taken together with the nitrogen atom to which each pair is attached, form a 4- to 6-membered heterocycloalkyl ring, which may contain a second ring heteroatom selected from N, O and S, and which is optionally substituted with one or two substituents independently selected from the group consisting of $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
$R^{14}$ and $R^{16}$ are hydrogen or $(C_1-C_4)$-alkyl,
$R^{15}$, $R^{17}$, $R^{18}$ and $R^{19}$ are each selected from the group consisting of $(C_1-C_6)$-alkyl, $(C_3-C_6)$-cycloalkyl, phenyl, 4- to 6-membered heterocycloalkyl and 5- or 6-membered heteroaryl, wherein
  (i) said $(C_3-C_6)$-cycloalkyl, phenyl, 4- to 6-membered heterocycloalkyl and 5- or 6-membered heteroaryl are optionally substituted with one or two substituents independently selected from the group consisting of fluoro, chloro, difluoromethyl, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
  and
  (ii) said $(C_1-C_6)$-alkyl is optionally substituted with one or two substituents independently selected from the group consisting of fluoro, trifluoromethyl, hydroxy, $(C_1-C_4)$-alkoxy, amino, mono-$(C_1-C_4)$-alkylamino, di-$(C_1-C_4)$-alkylamino, mono-$(C_1-C_4)$-alkylaminocarbonyl, di-$(C_1-C_4)$-alkylaminocarbonyl, $(C_3-C_6)$-cycloalkyl, phenyl, 4- to 6-membered heterocycloalkyl and 5- or 6-membered heteroaryl,
    wherein said $(C_3-C_6)$-cycloalkyl, phenyl, 4- to 6-membered heterocycloalkyl and 5- or 6-membered heteroaryl substituents in turn are optionally substituted with one or two residues independently selected from the group consisting of fluoro, chloro, trifluoromethyl, $(C_1-C_4)$-alkyl, oxo, hydroxy, $(C_1-C_4)$-alkoxy, amino, mono-$(C_1-C_4)$-alkylamino and di-$(C_1-C_4)$-alkylamino,
or
$R^{16}$ and $R^{17}$ are joined and, taken together with the nitrogen atom and $SO_2$ group to which they are attached, form a heterocyclic moiety of the formula

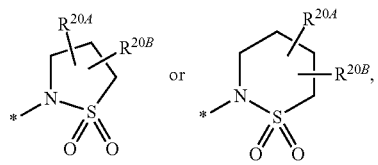

wherein * denotes the point of attachment to the indazole moiety,
and
$R^{20A}$ and $R^{20B}$ are independently hydrogen or methyl,
$R^2$ is hydrogen, fluoro or chloro,
$R^3$ is cyano or a group of the formula —$C(=O)$—$OR^{21}$ or —$C(=O)$—$NR^{22}R^{23}$, wherein $R^{21}$ is $(C_1-C_4)$-alkyl, and $R^{22}$ and $R^{23}$ are independently selected from the group consisting of hydrogen and $(C_1-C_4)$-alkyl, $R^4$ is $(C_1-C_4)$-alkyl optionally substituted with up to three fluoro atoms, or is amino, $R^5$ is hydrogen or $(C_1-C_4)$-alkyl optionally substituted with one or two substituents independently selected from the group consisting of hydroxy, $(C_1-C_4)$-alkoxy, amino, mono-$(C_1-C_4)$-alkylamino, di-$(C_1-C_4)$-alkylamino and 4- to 6-membered heterocycloalkyl, $R^6$ and $R^7$ are independently hydrogen or methyl, and either (a)

A is O, S or $S(=O)_2$ and m is 1 or 2, or (b)

A is $N(R^{24})$, wherein $R^{24}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, mono-$(C_1-C_4)$-alkylamino and di-$(C_1-C_4)$-alkylamino, and m is 1 or 2, in which case $R^5$ and $R^6$, in addition to the meanings specified above, may also be taken together and form an oxo group, or (c)

A is $-C(=O)-N(R^{25})-**$, wherein

** denotes the point of attachment to the $CR^5R^6$ group, and $R^{25}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, mono-$(C_1-C_4)$-alkylamino and di-$(C_1-C_4)$-alkylamino, and m is 0 or 1.

3. The compound of formula (I) according to claim 1, wherein $R^1$ is selected from the group consisting of $(C_1-C_4)$-alkyl, $(C_3-C_6)$-cycloalkyl and 5- or 6-membered heterocycloalkyl, wherein (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino, and (ii) said $(C_1-C_4)$-alkyl is optionally substituted with one or two substituents independently selected from the group consisting of hydroxy, methoxy, ethoxy, amino, methylamino, ethylamino, dimethylamino, diethylamino, $(C_3-C_6)$-cycloalkyl and 5- or 6-membered heterocycloalkyl, wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or $R^1$ is a group of the formula $-NR^8R^9$, $-C(=O)-NR^{10}R^{11}$, $-SO_2-NR^{12}R^{13}$, $-NR^{14}-C(=O)-R^{15}$, $-NR^{16}-SO_2-R^{17}$, $-OR^{18}$ or $-S(=O)_n-R^{19}$, wherein n is 0 or 2, $R^8$, $R^{10}$ and $R^{12}$ are each hydrogen or $(C_1-C_4)$-alkyl which is optionally substituted with hydroxy, methoxy, ethoxy, amino, methylamino, ethylamino, dimethylamino or diethylamino, $R^9$, $R^{11}$ and $R^{13}$ are each selected from the group consisting of hydrogen, $(C_1-C_4)$-alkyl, $(C_3-C_6)$-cycloalkyl and 5- or 6-membered heterocycloalkyl, wherein (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino, and (ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl, wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino, or $R^8$ and $R^9$, $R^{10}$ and $R^{11}$, $R^{12}$ and $R^{13}$ in pairs are joined and, taken together with the nitrogen atom to which each pair is attached, form a 5- or 6-membered heterocycloalkyl ring, which may contain a second ring heteroatom selected from N and O, and which is optionally substituted with one or two substituents independently selected from the group consisting of methyl, ethyl, oxo, hydroxy, methoxy, ethoxy, amino, methylamino, ethylamino, dimethylamino and diethylamino, $R^{14}$ and $R^{16}$ are hydrogen, methyl or ethyl, $R^{15}$, $R^{17}$, $R^{18}$ and $R^{19}$ are each selected from the group consisting of $(C_1-C_4)$-alkyl, $(C_3-C_6)$-cycloalkyl and 5- or 6-membered heterocycloalkyl, wherein (i) said $(C_3-C_6)$-cycloalkyl and 5- or 6-membered heterocycloalkyl are optionally substituted with one or two substituents independently selected from the group consisting of fluoro, methyl, ethyl, oxo, hydroxy, methoxy, ethoxy, amino, methylamino, ethylamino, dimethylamino and diethylamino, and (ii) said $(C_1-C_4)$-alkyl is optionally substituted with one or two substituents independently selected from the group consisting of fluoro, trifluoromethyl, hydroxy, methoxy, ethoxy, amino, methylamino, ethylamino, dimethylamino, diethylamino, $(C_3-C_6)$-cycloalkyl and 5- or 6-membered heterocycloalkyl, wherein said $(C_3-C_6)$-cycloalkyl and 5- or 6-membered heterocycloalkyl substituents in turn are optionally substituted with one or two residues independently selected from the group consisting of fluoro, methyl, ethyl, oxo, hydroxy, methoxy, ethoxy, amino, methylamino, ethylamino, dimethylamino and diethylamino,
or
$R^{16}$ and $R^{17}$ are joined and, taken together with the nitrogen atom and $SO_2$ group to which they are attached, form a heterocyclic moiety of the formula wherein * denotes the point of attachment to the indazole moiety,
$R^2$ is hydrogen or fluoro,
$R^3$ is cyano,
$R^4$ is methyl, trifluoromethyl or amino,
$R^5$ is hydrogen or $(C_1-C_4)$-alkyl optionally substituted with one or two substituents independently selected from the group consisting of hydroxy, amino, methylamino, ethylamino, dimethylamino and diethylamino,
$R^6$ and $R^7$ are hydrogen,
and either (a)
  A is O
  and
  m is 1,
or (b)
  A is $N(R^{24})$, wherein
    $R^{24}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, methylamino, ethylamino, dimethylamino and diethylamino,
  and
  m is 1,
  in which case
  $R^5$ and $R^6$, in addition to the meanings specified above, may also be taken together and form an oxo group,
or (c)
  A is $-C(=O)-N(R^{25})-$**, wherein
    ** denotes the point of attachment to the $CR^5R^6$ group,
    and
    $R^{25}$ is hydrogen, $(C_1-C_4)$-alkyl or $(C_3-C_6)$-cycloalkyl, wherein said $(C_1-C_4)$-alkyl and $(C_3-C_6)$-cycloalkyl are optionally substituted with one or two substituents independently selected from the group consisting of hydroxy, amino, methylamino, ethylamino, dimethylamino and diethylamino,
  and
  m is 0.

4. The compound of formula (I) according to claim 1, wherein
$R^1$ is selected from the group consisting of $(C_1-C_4)$-alkyl, phenyl and pyridyl, wherein said phenyl and pyridyl are optionally substituted with one or two substituents independently selected from the group consisting of fluoro, chloro, methyl and trifluoromethyl,
$R^2$ is hydrogen or fluoro,
$R^3$ is cyano,
$R^4$ is methyl,
$R^5$, $R^6$ and $R^7$ are hydrogen,
A is O,
and
m is 1.

5. A process for preparing a compound of formula (I) as defined in claim 1, characterized in that a compound of formula (II)

(II)

wherein m, A, $R^3$, $R^5$, $R^6$ and $R^7$ have the meanings indicated in claim 1,
is reacted in a protic solvent with acid catalysis either
[A] with a compound of formula (III)

(III)

wherein $R^1$, $R^2$ and $R^4$ have the meanings indicated in claim 1,
to give a compound of formula (I),
or
[B] with a compound of formula (IV)

(IV)

wherein $R^2$ and $R^4$ have the meanings indicated in claim 1,
and
X represents a leaving group,
to yield an intermediate compound of formula (V)

(V)

[Structure: indazole-HN-N with X, R², NC, R³, R⁴, R⁵, R⁶, N, R⁷, A, m]

wherein m, A, X, R², R³, R⁴, R⁵, R⁶ and R⁷ have the meanings described above,
which is then coupled under transition metal catalysis either
[B-1] with a compound of formula (VI)

$R^{14}$—H  (VI), wherein
$R^{14}$ represents an N-, O- or S-linked $R^1$ residue of the formula —$NR^8R^9$, —$OR^{18}$ or —$S(=O)_n$—$R^{19}$, respectively, as defined in claim 1,
to give a compound of formula (I-A)

(I-A)

[Structure with $R^{14}$]

wherein m, A, $R^{14}$, R², R³, R⁴, R⁵, R⁶ and R⁷ have the meanings described above,
or
[B-2] with a compound of formula (XIV)

$R^{1B}$-M  (XIV), wherein
$R^{1B}$ represents an optionally substituted C-linked $R^1$ residue selected from the group consisting of ($C_1$-$C_6$)-alkyl, ($C_3$-$C_7$)-cycloalkyl, phenyl, 4- to 7-membered heterocycloalkyl and 5- to 10-membered heteroaryl, as defined in claim 1,
and
M represents a —$B(OR^{26})_2$, —MgHal, —ZnHal or —$Sn(R^{27})_3$ group, wherein
Hal is chloro, bromo or iodo,
$R^{26}$ is hydrogen or ($C_1$-$C_4$)-alkyl, or both $R^{26}$ residues together form a —$(CH_2)_2$—, —$C(CH_3)_2$— $C(CH_3)_2$—, —$(CH_2)_3$— or —$CH_2$—$C(CH_3)_2$—$CH_2$— bridge,
and
$R^{27}$ is ($C_1$-$C_4$)-alkyl,
to yield a compound of formula (I-B)

(I-B)

[Structure with $R^{1B}$]

wherein m, A, $R^{1B}$, R², R³, R⁴, R⁵, R⁶ and R⁷ have the meanings described above,
optionally followed by (i) separating the compound (I), (I-A) or (I-B) into its enantiomers and/or diastereomers, and/or (ii) converting the compound (I), (I-A) or (I-B) into a hydrate, solvate, salt and/or hydrate or solvate of a salt by treatment with the corresponding solvents and/or acids or bases.

6. A pharmaceutical composition comprising a therapeutic agent, which is a compound as defined in claim 1, and a pharmaceutically acceptable excipient.

7. The pharmaceutical composition of claim 6 further comprising one or more additional therapeutic agents.

8. The pharmaceutical composition of claim 7, wherein the additional therapeutic agent is an anti-tumor agent.

9. A method of treating a cell proliferative disorder mediated by c-Met, comprising administering to a mammal in need thereof a therapeutically effective amount of one or more compounds as defined in claim 1.

10. The method of claim 9, wherein the cell proliferative disorder is a cancer.

11. The method of claim 10, wherein the cancer is a cancer of the breast, respiratory tract, brain, reproductive organs, digestive tract, urinary tract, eye, liver, skin, head or neck, thyroid, parathyroid, or a distant metastasis of a solid tumor.

12. The method of claim 10, wherein the compound is administered in conjunction with surgery or radiation therapy.

13. The process of claim 5, wherein X is chloro, bromo or iodo.

14. A method of treating a cell proliferative disorder mediated by c-Met, comprising administering to a mammal in need thereof a therapeutically effective amount of a pharmaceutical composition as defined in claim 6.

15. The method of claim 14, wherein the cell proliferative disorder is a cancer of the breast, respiratory tract, brain, reproductive organs, digestive tract, urinary tract, eye, liver, skin, head or neck, thyroid, parathyroid, or a distant metastasis of a solid tumor.

16. The method of claim 14, wherein the pharmaceutical composition is administered in conjunction with surgery or radiation therapy.

17. A method of treating a cell proliferative disorder mediated by c-Met, comprising administering to a mammal in need thereof a therapeutically effective amount of a pharmaceutical composition as defined in claim 8.

18. The method of claim 17, wherein the cell proliferative disorder is a cancer of the breast, respiratory tract, brain, reproductive organs, digestive tract, urinary tract, eye, liver, skin, head or neck, thyroid, parathyroid, or a distant metastasis of a solid tumor.

19. The method of claim 17, wherein the pharmaceutical composition is administered in conjunction with surgery or radiation therapy.

* * * * *